United States Patent [19]
Lassen et al.

[11] Patent Number: 6,060,298
[45] Date of Patent: May 9, 2000

[54] PENIOPHORA PHYTASE

[75] Inventors: Søren Flensted Lassen, Copenhagen Ø; Lisbeth Bech, Hillerød; Claus Crone Fuglsang, Nivå; Anders Ohmann, Brønshøj; Jens Breinholt, Bagsværd; Peter Rahbet Østergaard, Virum, all of Denmark

[73] Assignee: Novo Nordisk A/S, Bagsvaerd, Denmark

[21] Appl. No.: 08/989,358

[22] Filed: Dec. 12, 1997

Related U.S. Application Data

[60] Provisional application No. 60/046,081, May 9, 1997.

[30] Foreign Application Priority Data

Dec. 20, 1996 [DK] Denmark ................. 1481/96
May 7, 1997 [DK] Denmark ................. 0529/97

[51] Int. Cl.[7] ................. C12N 9/16; C12N 1/14; C12N 15/00; C12P 19/00
[52] U.S. Cl. ................. 435/196; 435/196; 435/320.1; 435/72; 435/254.1; 424/94.1; 424/94.6
[58] Field of Search ................. 435/196, 320.1, 435/72, 254.1; 424/94.1, 94.6

[56] References Cited

U.S. PATENT DOCUMENTS 5,123,203  6/1992  Hiromoto ................. 47/1.1

FOREIGN PATENT DOCUMENTS 684313  11/1995  European Pat. Off. .
WO 94/03610  2/1994  WIPO .

OTHER PUBLICATIONS

Howson et al., (1983) Production of phytate–hydrolysing enzyme by some fungi. Enzyme Microb. Technol. 5:377–382.

EMBL, Database GenBank/DDBJ, Accession No. R88623, "Fungal DNA sequences encoding polypeptide(s) with phytase activity—useful for conversion of phytate to inositol and inorganic phosphate in animal manure"; & EP A2 684313, Mar. 26, 1996.

Quaglia et al., (1995) Biomass and hydrolytic and oxidative enzymes production by fungal growth on wheat milling by–products. Die Nahrung. 39 (5/6) p. 483–489.

*Primary Examiner*—Ponnathapu Achutamurthy
*Assistant Examiner*—Peter P. Tung
*Attorney, Agent, or Firm*—Steve T. Zelson, Esq.; Reza Green, Esq.

[57] ABSTRACT

The present invention relates to an isolated polypeptide exhibiting phytase activity, the corresponding cloned DNA sequences, a process for preparing the polypeptide, and the use thereof for a number of industrial applications, in particular in animal feed. The novel phytase is derived from *Peniophora lycii* and has some interesting features, such as high initial affinity for the 6-position of phytic acid, a high intial rate of liberating phosphate from phytic acid and an exceptionally high specific activity.

11 Claims, 13 Drawing Sheets

Temperature profile of Peniophora phytase
0.1 M Na-acetate, 5mM phytate, pH 5.5, 30 min Temperature stability of Peniohora phytase—preincubation 60 min in 0.1 M Na-acetate pH 5.5

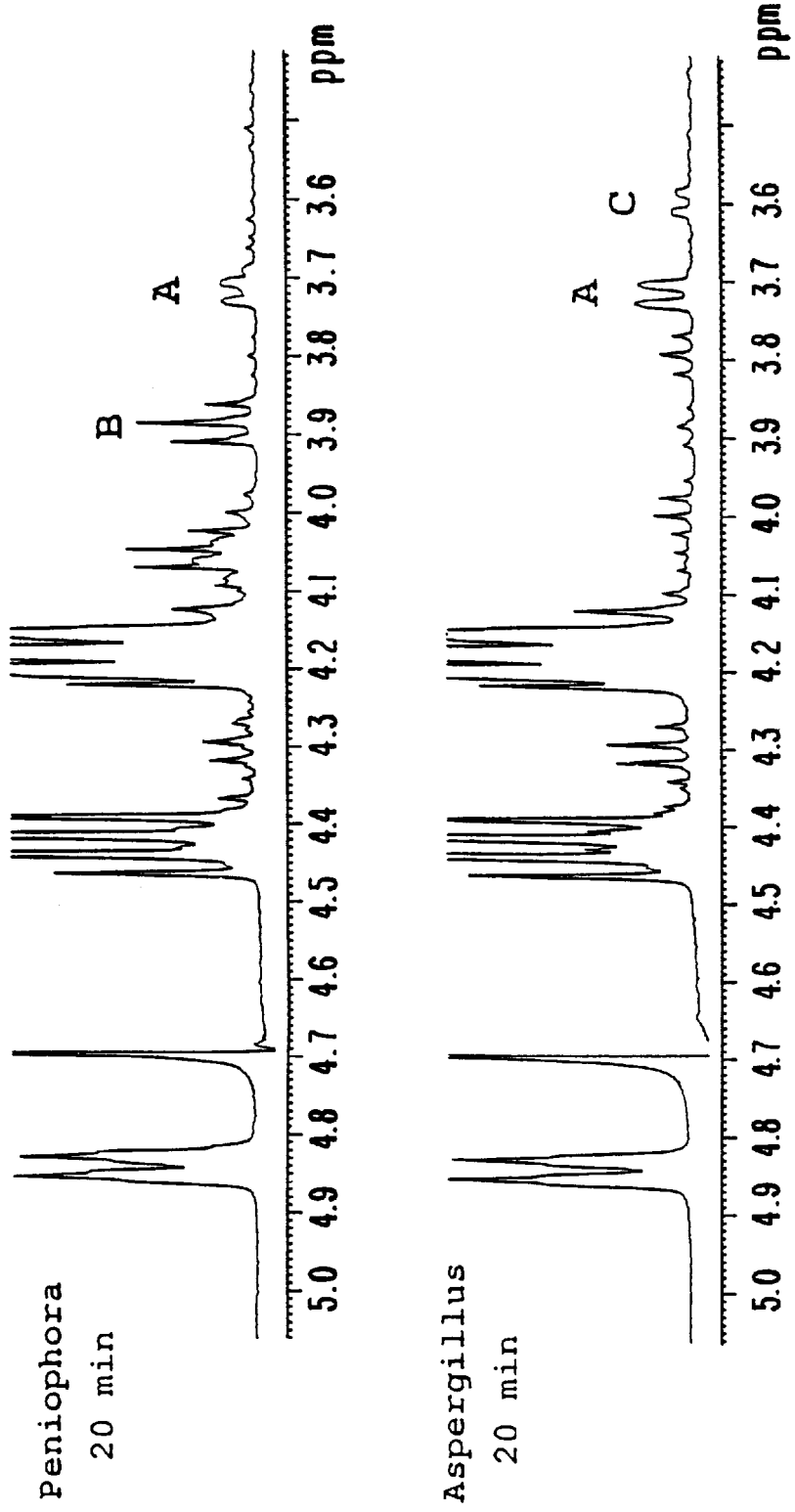

PENIOPHORA PHYTASE

CROSS-REFERENCE TO RELATED APPLICATIONS

This application claims priority under 35 U.S.C. 119 of U.S. application serial number 60/046,081 filed May 9, 1997 and of Danish applications 1481/96 filed Dec. 20, 1996, and 0529/97 filed May 7, 1997, the contents of which are fully incorporated herein by reference.

FIELD OF INVENTION

The present invention relates to an isolated polypeptide exhibiting phytase activity, the corresponding cloned DNA sequences, a process for preparing the polypeptide, and the use thereof for a number of industrial applications, in particular in animal feed.

BACKGROUND OF THE INVENTION

Phytic acid or myo-inositol 1,2,3,4,5,6-hexakis dihydrogen phosphate (or for short myo-inositol hexakisphosphate) is the primary source of inositol and the primary storage form of phosphate in plant seeds. In fact, it is naturally formed during the maturation of seeds and cereal grains. In the seeds of legumes it accounts for about 70% of the phosphate content and is structurally integrated with the protein bodies as phytin, a mixed potassium, magnesium and calcium salt of inositol. Seeds, cereal grains and legumes are important components of food and feed preparations, in particular of animal feed preparations. But also in human food cereals and legumes are becoming increasingly important.

The phosphate moieties of phytic acid chelates divalent and trivalent cations such as metal ions, i.a. the nutritionally essential ions of calcium, iron, zinc and magnesium as well as the trace minerals mangane, copper and molybdenum.

Besides, the phytic acid also to a certain extent binds proteins by electrostatic interaction. At a pH below the isoelectric point, pI, of the protein, the positively charged protein binds directly with phytate. At a pH above pI, the negatively charged protein binds via metal ions to phytate.

Phytic acid and its salts, phytates, are often not metabolized, since they are not absorbable from the gastro intestinal system, i.e. neither the phosphorous thereof, nor the chelated metal ions, nor the bound proteins are nutritionally available.

Accordingly, since phosphorus is an essential element for the growth of all organisms, food and feed preparations need to be supplemented with inorganic phosphate. Quite often also the nutritionally essential ions such as iron and calcium, must be supplemented. And, besides, the nutritional value of a given diet decreases, because of the binding of proteins by phytic acid. Accordingly, phytic acid is often termed an anti-nutritional factor.

Still further, since phytic acid is not metabolized, the phytate phosphorus passes through the gastrointestinal tract of such animals and is excreted with the manure, resulting in an undesirable phosphate pollution of the environment resulting e.g. in eutrophication of the water environment and extensive growth of algae.

Phytic acid or phytates, said terms being, unless otherwise indicated, in the present context used synonymously or at random, are degradable by phytases.

In most of those plant seeds which contain phytic acid, endogenous phytase enzymes are also found. These enzymes are formed during the germination of the seed and serve the purpose of liberating phosphate and, as the final product, free myo-inositol for use during the plant growth.

When ingested, the food or feed component phytates are in theory hydrolyzable by the endogenous plant phytases of the seed in question, by phytases stemming from the microbial flora in the gut and by intestinal mucosal phytases. In practice, however the hydrolyzing capability of the endogenous plant phytases and the intestinal mucosal phytases, if existing, is far from sufficient for increasing significantly the bioavailbility of the bound or constituent components of phytates. However, when the process of preparing the food or feed involve germination, fermentation or soaking, the endogenous phytase might contribute to a greater extent to the degradation of phytate.

In ruminant or polygastric animals such as horses and cows the gastro intestinal system hosts microorganisms capable of degrading phytic acid. However, this is not so in monogastric animals such as human beings, poultry and swine. Therefore, the problems indicated above are primarily of importance as regards such monogastric animals.

The production of phytases by plants as well as by microorganisms has been reported. Amongst the microorganisms, phytase producing bacteria as well as phytase producing fungi are known.

From the plant kingdom, e.g. a wheat-bran phytase is known (Thomlinson et al, Biochemistry, 1 (1962), 166–171). An alkaline phytase from lilly pollen has been described by Barrientos et al, Plant. Physiol., 106 (1994), 1489–1495.

Amongst the bacteria, phytases have been described which are derived from *Bacillus subtilis* (Paver and Jagannathan, 1982, Journal of *Bacteriology* 151:1102–1108) and Pseudomonas (Cosgrove, 1970, *Australian Journal of Biological Sciences* 23:1207–1220). Still further, a phytase from *E. coli* has been purified and characterized by Greiner et al, Arch. Biochem. Biophys., 303, 107–113, 1993). However, this enzyme is probably an acid phosphatase.

Phytase producing yeasts are also described, such as *Saccharomyces cerevisiae* (Nayini et al, 1984, *Lebensmittel Wissenschaft und Technologie* 17:24–26. However, this enzyme is probably a myo-inositol monophosphatase (Wodzinski et al, Adv. Appl. Microbiol., 42, 263–303). AU-A-24840/95 describes the cloning and expression of a phytase of the yeast *Schwanniomyces occidentalis*.

There are several descriptions of phytase producing filamentous fungi, however only belonging to the fungal phyllum of Ascomycota (ascomycetes). In particular, there are several references to phytase producing ascomycetes of the Aspergillus genus such as *Aspergillus terreus* (Yamada et al., 1986, *Agric. Biol. Chem.* 322:1275–1282). Also, the cloning and expression of the phytase gene from *Aspergillus niger* var. awamori has been described (Piddington et al., 1993, Gene 133:55–62). EP 0 420 358 describes the cloning and expression of a phytase of *Aspergillus ficuum* (niger). EP 0 684 313 describes the cloning and expression of phytases of the ascomycetes *Myceliophthora thermophila* and *Aspergillus terreus*.

NOMENCLATURE AND POSITION SPECIFICITY OF PHYTASES

In the present context a phytase is an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate. In the following, for short, the above compounds are sometimes referred to as IP6, I, IP1, IP2, IP3, IP4, IP5 and P, respectively. This means that by action of a phytase, IP6 is degraded into P+ one or more of the components IP5, IP4, IP3, IP2, IP1 and I. Alternatively, myo-inositol carrying in total n phosphate groups attached to positions p, q, r, . . . is denoted Ins(p,q,r, . . . )$P_n$. For convenience Ins(1,2,3,4,5,6)$P_6$ (phytic acid) is abbreviated PA.

According to the Enzyme nomenclature database ExPASy (a repository of information relative to the nomenclature of enzymes primarily based on the recommendations of the Nomenclature Committee of the International Union of Biochemistry and Molecular Biology (IUBMB) describing each type of characterized enzyme for which an EC (Enzyme Commission) number has been provided), two different types of phytases are known: A so-called 3-phytase (myo-inositol hexaphosphate 3-phosphohydrolase, EC 3.1.3.8) and a so-called 6-phytase (myo-inositol hexaphosphate 6-phosphohydrolase, EC 3.1.3.26). The 3-phytase hydrolyses first the ester bond at the 3-position, whereas the 6-phytase hydrolyzes first the ester bond at the 6-position.

Inositolphosphate nomenclature

Considering the primary hydrolysis products of a phytase acting on phytic acid, some of the resulting esters are diastereomers and some are enantiomers. Generally, it is easier to discriminate between diastereomers, since they have different physical properties, whereas it is much more difficult to discriminate between enantiomers which are mirror images of each other.

Thus, Ins(1,2,4,5,6)$P_5$ (3-phosphate removed) and Ins(1,2,3,4,5)$P_5$ (6-phosphate removed) are diastereomers and easy to discriminate, whereas Ins(1,2,4,5,6)$P_5$ (3-phosphate removed) and Ins(2,3,4,5,6) $P_5$ (1-phosphate removed) are enantiomers. The same holds true for the pair Ins(1,2,3,4,5)$P_5$ (6-phosphate removed) and Ins(1,2,3,5,6)$P_5$ (4-phosphate removed). Accordingly, of the 6 pentaphosphate esters resulting from the first step of the phytase catalyzed hydrolysis of phytic acid, you can only discriminate easily between those esters in which the 2-, 3-, 5- and 6-phosphate has been removed, i.e. you have four diastereomers only, each of the remaining two esters being an enantiomer of one each of these compounds (4- and 6- are enantiomers, as are 1- and 3-).

Use of lowest-locant rule

It should be noted here, that when using the notations Ins(2,3,4,5,6)$P_5$ and Ins(1,2,3,5,6)$P_5$, a relaxation of the previous recommendations on the numbering of the atoms of myo-inositol has been applied. This relaxation of the lowest-locant rule is recommended by the Nomenclature Committee of the International Union of Biochemistry (Biochem. J. (1989) 258, 1–2) whenever authors wish to bring out structural relationships.

In this lowest-locant rule, the L- and D-nomenclature is recommended: Inositolphosphate, phosphate esters of myo-inositol, are generally designated 1D- (or 1L-) -Ins(r,s,t,u,w,x)$P_n$, n indicating the numer of phosphate groups and the locants r,s,t,u,w and x, their positions. The positions are numbered according to the Nomenclature Committee of the International Union of Biochemistry (NC-IUB) cited above (and the references herein), and 1D or 1L is used so as to make a substituent have the lowest possible locant or number ("lowest-locant rule").

Phytase specificity

As said above, phytases are divided according to their specificity in the initial hydrolysis step, viz. according to which phosphate-ester group is hydrolyzed first.

As regards the specificity of known phytases, plant phytases are generally said to be 6-phytases. However the lilly pollen phytase is said to be a 5-phytase. The microorganism derived phytases are mainly said to be 3-phytases. E.g. the ExPASy is database mentioned above refers for 3-phytases to four phytases of Aspergillus awamori (strain ALK0243) and *Aspergillus niger* (strain NRRL 3135) (Gene 133:55–62 (1993) and Gene 127:87–94 (1993)).

Using now the D-/L-notation (in which the D- and L-configuration refer to the 1-position), the wheat-bran phytase hydrolyzes first the phosphate ester group in the L-6 position (=D-4), whereas the 3-phytases hydrolyzes first the phosphate ester group in position D-3 (=L-1).

The specificity can be examined in several ways, e.g by HPLC or by NMR spectroscopy. These methods, however, do not immediately allow the discrimination between hydrolysis of e.g. the phosphate-ester groups in positions D-6 and L-6, since the products of the hydrolysis, D-Ins(1,2,3,4,5)$P_5$ and L-Ins(1,2,3,4,5) $P_5$, are enantiomers (mirror images), and therefore have identical NMR spectres.

In other words, in the present context a 6-phytase means either of a L-6- or a D-6-phytase or both, viz. a phytase being a L-6-phytase, a D-6-phytase or a ((D-6-)+(L-6-))-phytase (having both activities). The latter is sometimes also designated D/L-6-phytase.

SUMMARY OF THE INVENTION

It is an object of the present invention to provide alternative phytases, in particular with superior properties such as increased heat stability or faster release of phosphate from phytate, and which can be produced in commercially useful quantities.

The present inventors have surprisingly found that an enzyme exhibiting phytase activity may be obtained from a fungal strain of the order Stereales in particular of the family Peniophoraceae, especially from the genus Peniophora, more specifically of the strain *Peniophora lycii*, and have succeeded in cloning a DNA sequence encoding said enzyme. The DNA sequence and the deduced amino acid sequence are listed in the sequence listing as SEQ ID No. 1 and 2, respectively.

As further outlined in the experimental section below, this novel phytase has surprisingly turned up to have a faster initial liberation of phosphorous from phytic acid, in particular as compared to a known phytase (*Aspergillus niger phytase*, Phytase Novo®). This has been shown in an application relevant corn assay at pH 3.5 and pH 5.5 as well as in NMR-studies.

Still further, the phytase of the invention has turned up to have an interestingly different degradation profile. At pH 3.5 it belongs to a novel class of phytases exhibiting high initial affinity for the 6- as well as the 3-position of phytic acid, in other words it is neither a 3-phytase nor a 6-phytase but less position specific than hitherto reported for any known phytase. At pH 5.5, however, it should be classified as a 6-phytase.

Also the specific activity of the Peniophora lycii phytase is at a very high level, viz. more than 200, preferably more than 400, especially more than 600, in particular more than 800, most preferably about 1000 FYT/mg, reference being had to Example 4a. This is rather unexpected, at least for fungal phytases (the known Aspergillus phytase having a specific activity of only approximately 180 FYT/mg).

The order of Stereales belongs to the fungal class of Hymenomycetes and the fungal phyllum of Basidiomycota. Known phytase producing fungi belong to the phyllum of Ascomycota.

In a first aspect, the invention relates to an isolated polypeptide having phytase activity and having the amino acid sequence of SEQ ID NO 2 or the sequence of amino acid no. 31 to 439 thereof, or an amino acid sequence which is at least 70% homologous to either of these sequences.

In further aspects, the invention provides cloned DNA sequences encoding the above polypeptides, as well as vectors and host cells comprising these cloned DNA sequences.

Within the scope of the invention, in a still further aspect, is the use of the phytase of the invention for liberating inorganic phosphate from phytic acid, as well as some more specific uses, and compositions, in particular food and feed preparations and additives comprising the phytase of the invention.

Generally, terms and expressions as used herein are to be interpreted as is usual in the art. In cases of doubt, however, the definitions of the present description might be useful.

GENERAL DEFINITIONS

By the expression "an isolated polypeptide/enzyme having/exhibiting phytase activity" or "an isolated phytase" is meant any peptide or protein having phytase activity (vide below) and which is essentially free of other non-phytase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE. Sometimes such polypeptide is alternatively referred to as a "purified" phytase.

The definition of "an isolated polypeptide" also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

The expression "polypeptide or enzyme exhibiting phytase activity" or "phytase" is intended to cover any enzyme capable of effecting the liberation of inorganic phosphate or phosphorous from various myo-inositol phosphates. Examples of such myo-inositol phosphates (phytase substrates) are phytic acid and any salt thereof, e.g. sodium phytate or potassium phytate or mixed salts. Also any stereoisomer of the mono-, di-, tri-, tetra- or penta-phosphates of myo-inositol might serve as a phytase substrate.

In accordance with the above definition, the phytase activity can be determined using any assay in which one of these substrates is used. In the present context (unless otherwise specified) the phytase activity is determined in the unit of FYT, one FYT being the amount of enzyme that liberates 1 μmol inorganic ortho-phosphate per min. under the following conditions: pH 5.5; temperature 37° C.; substrate: sodium phytate ($C_6H_{24}O_{24}P_6Na_{12}$) in a concentration of 0.0050 mol/l. Suitable phytase assays are described in the experimental part.

"Polypeptide homology" or "amino acid homology" is determined as the degree of identity between two sequences. The homology may suitably be determined by means of computer programs known in the art such as GAP provided in the GCG version 8 program package (Program Manual for the Wisconsin Package, Version 8, Genetics Computer Group, 575 Science Drive, Madison, Wis., USA 53711) (Needleman, S. B. and Wunsch, C. D., (1970), Journal of Molecular Biology, 48, 443–453. Using GAP s with the following settings for polypeptide sequence comparison: GAP creation penalty of 5.0 and GAP extension penalty of 0.3.

In the present context a "6-phytase" means a phytase which hydrolyzes first the 6-position in phytic acid or has a preference for these positions (plural is used since this term covers two positions). In particular, more than 50% of the hydrolysis product of the first step is $Ins(1,2,3,4,5)P_5$ and/or $Ins(1,2,3,5,6)P_5$. Preferably these two compounds comprise at least 60%, more preferably at least 70%, still more preferably at least 80%, especially at least 90% and mostly preferred more than 95% of the product of the initial hydrolysis step of PA.

The other specificity terms such as e.g. "3-phytase," "(3+6)-phytase," "6D-phytase" and "6L-phytase" are to be interpreted correspondingly, including the same preferred embodiments.

The terms "a phytase encoding part of a DNA sequence cloned into a plasmid present in a deposited *E. coli* strain" and "a phytase encoding part of the corresponding DNA sequence presented in the sequence listing" are presently believed to be identical, and accordingly they may be used interchangeably.

Primarily, the term "a phytase encoding part" used in connection with a DNA sequence means that region of the DNA sequence which is translated into a polypeptide sequence having phytase activity. Often this is the region between a first "ATG" start codon ("AUG" codon in mRNA) and a stop codon ("TAA", "TAG" or "TGA") first to follow.

However, the polypeptide translated as described above often comprises, in addition to a mature sequence exhibiting phytase activity, an N-terminal signal sequence and/or a pro-peptide sequence. Generally, the signal sequence guides the secretion of the polypeptide and the pro-peptide guides the folding of the polypeptide. For further information see Egnell, P. et al. Molecular Microbiol. 6(9):1115–19 (1992) or Stryer, L., "Biochemistry" W. H., Freeman and Company/ New York, ISBN 0-7167-1920-7. Therefore, the term "phytase encoding part" is also intended to cover the DNA sequence corresponding to the mature part of the translated polypeptide or to each of such mature parts, if several exist.

Still further, any fragment of such sequence encoding a polypeptide fragment, which still retains some phytase activity, is to be included in this definition.

A cloned DNA sequence or, alternatively, "a DNA construct," "a DNA segment" or "an isolated DNA sequence" refers to a DNA sequence which can be cloned in accordance with standard cloning procedures used in genetic engineering to relocate the DNA segment from its natural location to a different site where it will be replicated. The term refers generally to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The degree of identity or "homology" between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3.

Suitable experimental conditions for determining whether a given DNA or RNA sequence "hybridizes" to a specified nucleotide or oligonucleotide probe involves presoaking of the filter containing the DNA fragments or RNA to examine for hybridization in 5×SSC (Sodium chloride/Sodium citrate), (J. Sambrook, E. F. Fritsch, and T. Maniatis, 1989, *Molecular Cloning, A Laboratory Manual*, 2d edition, Cold Spring Harbor, New York) for 10 min, and prehybridization of the filter in a solution of 5×SSC, 5×Denhardt's solution (Sambrook et al. 1989), 0.5% SDS and 100 μg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6–13), $^{32}$P-dCTP-labeled (specific activity >1×10$^9$ cpm/μg) probe for 12 hours at approximately 45° C.

The filter is then washed twice for 30 minutes in 2 x SSC, 0.5% SDS at at least 55° C. (low stringency), at at least 60° C. (medium stringency), at at least 65° C. (medium/high stringency), at at least 70° C. (high stringency), or at at least 75° C. (very high stringency).

Molecules to which the oligonucleotide probe hybridizes under these conditions are detected using an x-ray film.

It has been found that it is possible to theoretically predict whether or not two given DNA sequences will hybridize under certain specified conditions.

Accordingly, as an alternative to the above described experimental method the determination whether or not an analogous DNA sequence will hybridize to the nucleotide probe described above, can be based on a theoretical calculation of the Tm (melting temperature) at which two heterologous DNA sequences with known sequences will hybridize under specified conditions (e.g. with respect to cation concentration and temperature).

In order to determine the melting temperature for heterologous DNA sequences (Tm(hetero)) it is necessary first to determine the melting temperature (Tm(homo)) for homologous DNA sequences.

The melting temperature (Tm(homo)) between two fully complementary DNA strands (homoduplex formation) may be determined by use of the following formula, Tm(homo)=81.5° C.+16.6(log M)+0.41(% GC)−0.61 (% form)−500/L ("Current protocols in Molecular Biology". John Wiley and Sons, 1995), wherein

| "M" | denotes the molar cation concentration in wash buffer, |
| "% GC" | % Guanine (G) and Cytosine (C) of total number of bases in the DNA sequence, |
| "% form" | % formamid in the wash buffer, and |
| "L" | the length of the DNA sequence. |

The Tm determined by the above formula is the Tm of a homoduplex formation (Tm(homo)) between two fully complementary DNA sequences. In order to adapt the Tm value to that of two heterologous DNA sequences, it is assumed that a 1% difference in nucleotide sequence between the two heterologous sequences equals a 1° C. decrease in Tm ("Current protocols in Molecular Biology". John Wiley and Sons, 1995). Therefore, the Tm(hetero) for the heteroduplex formation is found by subtracting the homology % difference between the analogous sequence in question and the nucleotide probe described above from the Tm(homo). The DNA homology percentage to be subtracted is calculated as described herein (vide supra).

The term "vector" is intended to include such terms/objects as "nucleic acid constructs," "DNA constructs," expression vectors" or "recombinant vectors."

The nucleic acid construct comprises a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature.

The term nucleic acid construct may be synonymous with the term expression cassette when the nucleic acid construct contains all the control sequences required for expression of a coding sequence of the present invention.

The term "coding sequence" as defined herein primarily comprises a sequence which is transcribed into mRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

In the expression vector, the DNA sequence encoding the phytase should be operably connected to a suitable promoter and terminator sequence. The promoter may be any DNA sequence which shows transcriptional activity in the host cell of choice and may be derived from genes encoding proteins which are either homologous or heterologous to the host cell. The procedures used to ligate the DNA sequences coding for the phytase, the promoter and the terminator and to insert them into suitable vectors are well known to persons skilled in the art (cf. e.g. Sambrook et al., (1989), Molecular Cloning. A Laboratory Manual, Cold Spring Harbor, N.Y.).

The recombinant expression vector may be any vector (e.g., a plasmid or virus) which can be conveniently subjected to recombinant DNA procedures and can bring about the expression of the nucleic acid sequence.

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

A "host cell" or "recombinant host cell" encompasses any progeny of a parent cell which is not identical to the parent cell due to mutations that occur during replication.

The cell is preferably transformed with a vector comprising a nucleic acid sequence of the invention followed by integration of the vector into the host chromosome.

"Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The host cell may be a unicellular microorganism, e.g., a prokaryote, or a non-unicellular microorganism, e.g., a eukaryote. Examples of a eukaryote cell is a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phylla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Reference is also had to Julich, 1981, Higher Taxa of Basidiomycetes and Hansen & Knudsen (Eds.), Nordic Macromycetes, vol. 2 (1992) and 3 (1997).

Fungal cells may be transformed by a process involving protoplast formation, transformation of the protoplasts, and regeneration of the cell wall in a manner known per se.

Preferred host cells are a strain of Fusarium, Trichoderma or Aspergillus, in particular a strain of *Fusarium graminearum, Fusarium venenatum, Fusarium cerealis*, Fusarium sp. having the identifying characteristic of Fusarium ATCC 20334, as further described in PCT/US/95/07743, *Trichoderma harzianum* or *Trichoderma reesei, Aspergillus niger* or *Aspergillus oryzae*.

BRIEF DESCRIPTION OF THE DRAWINGS

In the detailed description of the invention below, reference is had to the drawings, of which

DEPOSITIONS

Figure 1:
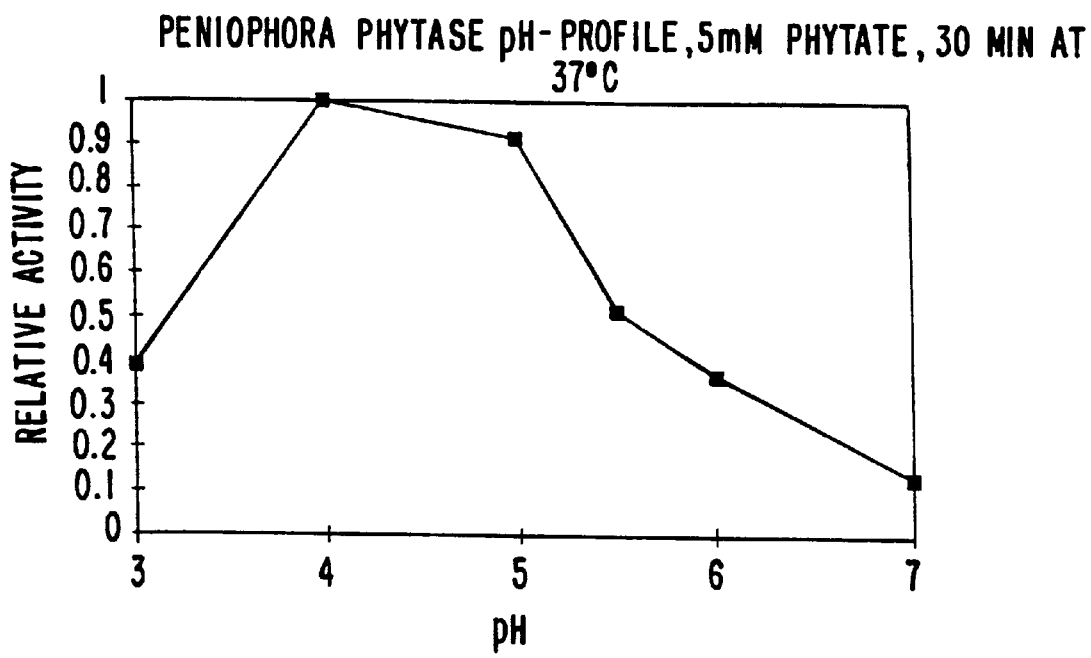
FIG. 1 is a pH-activity curve of the Peniophora phytase (5 mM phytate, 30 min. at 37° C.)

The isolated strain of *Peniophora lycii*, from which the phytase of the invention was obtained has been deposited according to the Budapest Treaty on the International Recognition of the Deposit of Microorganisms for the Purposes of Patent Procedure at the Centraalbureau voor Schimmelcultures, P.O. Box 273, 3740 AG Baarn, The Netherlands, (CBS), as follows:

Deposit date : Dec. 4 th of 1996

Depositor's ref. : NN006113

CBS No. : *Peniophora lycii* CBS No. 686.96

Still further, the expression plasmid (shuttle vector) pYES 2.0 comprising the full length cDNA sequences encoding this phytase of the invention has been transformed into a strain of *Escherichia coli* which was deposited according to the Budapest Treaty on the International Recognition of the Deposit of Microorganisms for the Purposes of Patent Procedure at the Deutsche Sammlung von Mikroorganismen und Zellkulturen GmbH., Mascheroder Weg 1b, D-38124 Braunschweig, Germany, (DSM), as follows:

Deposit date : Dec. 2nd of 1996

Depositor's ref. : NN 049282

DSM No. : *Escherichia coli* DSM No. 11312

DETAILED DESCRIPTION OF THE INVENTION

The homology of known phytases to the phytase of amino acid sequence SEQ ID NO 2 and the DNA sequence of SEQ ID NO 1 is as follows:

Homology (at amino acid and DNA-level, respectively) to the phytases of:

|                                       | Amino acid | DNA |
|---------------------------------------|------------|-----|
| *Aspergillus niger* (NRRL 3135):      | 41%        | 51% |
| *Aspergillus terreus* (strain 9A-1):  | 41%        | 53% |
| *Myceliophthora thermophila* (ATCC 48102): | 45%   | 54% |
| *Schwanniomyces occidentalis*:        | 26%        | 38% |
| *Escherichia coli* K12 (ATCC 33965):  | —          | 39% |

The "-" indicates no real recognition between the phytases of *P. lycii* and *E. coli*.

Accordingly, the *Peniophora phytase* is rather different from the known phytases, the closest related being the phytase of *Myceliophthora thermophila* (EP 0684313).

As described in more detail in the experimental part below, when expressed in Aspergillus, the *Peniophora phytase* has an N-terminal amino acid sequence of Leu-Pro-Ile-Pro-Ala-Gln-Asn-SEQ ID NO: 3 (amino acids no. 31–37 in SEQ ID NO 2). Accordingly the sequence of amino acids nos. 31–439 of SEQ ID No 2 is presently believed to be a mature phytase sequence.

Preferably, all amino acid homologies of the present application are at least 55%, or at least 60%, or at least 65%, especially at least 70%. Preferably, the degree of homology is at least 80%, more preferably at least 90%, still more preferably at least 95%, especially at least 97%.

The phytase polypeptide is obtainable from *Peniophora lycii* CBS 686.96 and has one or more of the following features:

(i) a pH-optimum of 3–6

(ii) a temperature optimum of 30–65° C.

(iii) stable for at least one hour at pH 3–9 and 40° C.

(iv) more than 75% residual activity after pre-incubation one hour at temperatures of 0–50° C.

(v) a molecular weight of the deglycosylated form of 43–53 kDa (vi) at least 20% residual activity after 60 minutes pre-incubation at 70° C.

(vii) an unfolding temperature as determined by DSC of 50–65° C.

Some alternative or more preferred ranges are listed below:

(i) a pH-optimum preferably of 3.5–5.5, more preferably 3.7–5.2, most preferably 3.8–5.0

(ii) a temperature optimum preferably of 35–62° C., more preferably around 37–58° C., possibly around 50° C.

(iii) preferably stable for at least one hour at 40° C. at pH 3–6, more preferably at pH 3–5

(iv) preferably at least 80% residual activity after incubation one hour at temperatures of 0–50° C. at pH 5.5, more preferably at least 90% residual activity after incubation one hour at temperatures of 0–50° C. at pH 5.5;

(v) The molecular weight of the deglycosylated form of the polypeptide according to SEQ ID NO 2 is calculated to 48 kDa. A polypeptide can be deglycosylated enzymatically or chemically and the molecular weight determined by e.g. Mass spectroscopy or on a SDS-PAGE gel. The chemical deglycosylation is described in "Carbohydrate analysis—a practical approach" by M. F. Chaplin & J. F. Kennedy (Eds.), IRL Press, Oxford, 1986, vide in particular Chapter V. For enzymatical deglycosylation the procedure indicated by the enzyme supplier is followed. Alternatively an apparent molecular weight Mr of approximately 67 kDa is determined relative to the migration of molecular weight markers in SDS-PAGE. This value of approximately 67 kDa is obtained when the enzyme is expressed in Aspergillus (vide the examples below).

(vi) preferably at least 30%, more preferably at least 40%, most preferably at least 50% residual activity after 60 minutes pre-incubation at 70° C., pH 5.5; or preferably at least 30%, more preferably at least 40%, most preferably at least 50% residual activity after pre-incubation one hour at temperatures of 60–80° C. at pH 5.5

(vii) preferably an unfolding temperature as determined by DSC of 55–62° C., more preferably of 58–62° C., still more preferably of approximately 60° C.

Alternatively, the features to follow are characteristic of the polypeptide: A pH optimum in the range 3–7, measured at 37° C.; more preferably a pH optimum in the range 4–6, measured at 37° C.; and even more preferably a pH optimum in the range 4.5–5.5, measured at 37° C.; and or at least 65% residual phytase activity after 20 minutes incubation at 70° C., measured relatively to the activity at 26° C.; more preferably at least 75% residual phytase activity after 20 minutes incubation at 70° C., measured relatively to the activity at 26° C.; and even more preferably at least 80% residual phytase activity after 20 minutes incubation at 70° C., measured relatively to the activity at 26° C.

It is presently contemplated that polypeptides of the invention are also obtainable from any strain of the class Hymenomycetes, preferably from the order Stereales, more preferably from strains of the genus Peniophora, and still more preferably from any strain of *Peniophora lycii*.

Preferably, the polypeptide of the invention is capable of refolding to regain at least 10%, preferably at least 20%, more preferably at least 30%, still more preferably at least 40% and most preferably at least 50% of its phytase activity after having been denatured.

One way of screening for such fungal polypeptides is as follows: The micro organism in question is plated onto phytate replication plates (vide Example 1, "Identification of positive colonies") and incubated at for instance 30 or 37° C. Phytase positive colonies are isolated, cultivated in shake flasks, and the supernatant is removed. The phytase activity of the supernatant is assayed before and following a thermal treatment of for instance 20 minutes at 70° C., by the method of Example 1 ("Test of *A. oryzae* transformants"). Those samples which are still phytase positive after incubation e.g. 20 minutes at 70° C. are either thermostable or capable of refolding to regain an important part of their phytase activity. The true thermostable ones may be excluded by following the methods of Example 5 or 6, i.e. assaying the residual activity following incubation at a number of temperatures in the relevant area to establish whether the residual activity drops and re-rises with increasing temperature.

This method is applicable by analogy to other microorganisms such as bacteria by using basal media and temperatures corresponding to the demands of the organisms in question.

The invention also relates to an isolated polypeptide exhibiting phytase activity which in use makes the PA substrate (the fully phosphorylated) disappear very early, in particular within 5 hours, preferably within 4 hours, more preferably within 3 hours, in particular within 2 hours, especially within one hour and very especially within ; hour (reference being had to Example 5 herein);

an isolated polypeptide exhibiting phytase activity and which liberates inorganic phosphate faster from phytic acid, in particular at pH 3.5 (reference being had to Example 6 herein); and the use of any of these four types of phytases, in particular in baking, dough making, the preparation of inositol or derivatives thereof, in food or feed, especially in animal feed or animal feed additives.

Claim 4 relates to nucleotide sequences of the phytases of the invention, in particular to DNA sequences.

For a definition of "hybridization," please refer to the section headed "General definition," which also lists some preferred hybridization conditions.

The degree of identity or homology between two nucleic acid sequences may be determined as described in the general definitions section. With respect to the homology part in feature (c) of claim 4, the degree of homology to the nucleic acid sequence set forth under heading (a) and (b) is at least about 55%, (still encoding an polypeptide exhibiting phytase activity). In particular, the homology is at least 60%, or at least 65%, especially at least 70%, preferably at least about 80%, more preferably at least about 90%, even more preferably at least about 95%, and most preferably at least about 97%. In particular, the degree of homology is based on a comparison with the entire sequences listed or their complementary strand or any of the sub-sequences thereof corresponding to a "mature" phytase.

Preferably, the conditions of hybridization (feature (d)) are of low, medium, medium/high, high or very high stringency.

The DNA sequence of the invention can also be cloned by any general method involving cloning, in suitable vectors, a cDNA library from any organism expected to produce the phytase of interest, transforming suitable yeast host cells with said vectors, culturing the host cells under suitable conditions to express any enzyme of interest encoded by a clone in the cDNA library, screening for positive clones by determining any phytase activity of the enzyme produced by such clones, and isolating the enzyme encoding DNA from such clones.

A general isolation method has been disclosed in WO 93/11249 and WO 94/14953. A detailed description of the screening methods is given in the experimental part.

The invention also relates generally to the use of the polypeptide according to any of claims 1–3 for liberating (or catalyzing the liberation of) inorganic phosphate from phytate or phytic acid. An alternative wording could be: for converting phytate to inorganic phosphate and (myo-inositol and/or mono-, di-, tri-, tetra-, penta-phosphate esters thereof). Within the scope of this claim is any process wherein the phytase of the invention excerts its phytase activity as previously defined.

More specific uses according to the invention are in human food or animal feed preparations or in additives for such preparations, wherein the phytase i.a. serves the purposes of (i) reducing the phytate level of manure, (ii) improving the digestibility, promoting the growth, or improving the food and feed utilization or its conversion efficiency, i.a. by making available proteins, which would otherwise have been bound by phytate, (iii) preventing malnutrition or diseases such as anemia caused by essential ions and phosphate lacking, i.e. improving the bioavailibility of minerals or increasing the absorption thereof, eliminating the need for adding supplemental phosphate and ions etc.

In particular, the phytases of the invention can also be used in chicken food to improve egg shell quality (reduction of losses due to breaking), cf. e.g. The Merck Veterinary Manual, (Seventh edition, Merck & CO., Inc., Rahway, N.J., U.S.A., 1991; p.1268); Jeroch et al; Bodenkultur Vol. 45, No. 4 pp. 361–368 (1994); Poultry Science, Vol. 75, No. 1 pp. 62–68 (1996); Canadian Journal of Animal Science Vol. 75, No. 3 pp. 439–444 (1995); Poultry Science Vol. 74, No. 5 pp. 784–787 (1995) and Poultry Science Vol. 73, No. 10 pp. 1590–1596 (1994).

A "feed" and a "food," respectively, means any natural or artificial diet, meal or the like or components of such meals intended or suitable for being eaten, taken in, digested, by an animal and a human being, respectively.

The phytase may exert its effect in vitro or in vivo, i.e. before intake or in the stomach of the individual, respectively. Also a combined action is possible.

A phytase composition according to the invention always comprises at least one phytase of the invention.

Generally, phytase compositions are liquid or dry.

Liquid compositions need not contain anything more than the phytase enzyme, preferably in a highly purified form. Usually, however, a stabilizer such as glycerol, sorbitol or mono propylen glycol is also added. The liquid composition may also comprise other additives, such as salts, sugars, preservatives, pH-adjusting agents, proteins, phytate (a phytase substrate). Typical liquid compositions are aqueous or oil-based slurries. The liquid compositions can be added to a food or feed after an optional pelleting thereof.

Dry compositions may be spray dried compositions, in which case the composition need not contain anything more than the enzyme in a dry form. Usually, however, dry compositions are so-called granulates which may readily be mixed with e.g. food or feed components, or more preferably, form a component of a pre-mix. The particle size of the enzyme granulates preferably is compatible with that of the other components of the mixture. This provides a safe and convenient mean of incorporating enzymes into e.g. animal feed.

Agglomeration granulates are prepared using agglomeration technique in a high shear mixer (e.g. Lödige) during which a filler material and the enzyme are co-agglomerated to form granules. Absorption granulates are prepared by having cores of a carrier material to absorp/be coated by the enzyme.

Typical filler materials are salts such as disodium sulphate. Other fillers are kaolin, talc, magnesium aluminium silicate and cellulose fibres. Optionally, binders such as dextrins are also included in agglomeration granulates.

Typical carrier materials are starch, e.g. in the form of cassava, corn, potato, rice and wheat. Salts may also be used.

Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

Additionally, phytase compositions may contain other substituents such as colouring agents, aroma compounds, stabilizers, vitamins, minerals, other feed or food enhancing enzymes etc. This is so in particular for the so-called pre-mixes.

A "food or feed additive" is an essentially pure compound or a multi component composition intended for or suitable for being added to food or feed. In particular it is a substance which by its intended use is becoming a component of a food or feed product or affects any characteristics of a food or feed is product. It is composed as indicated for phytase compositions above. A typical additive usually comprises one or more compounds such as vitamins, minerals or feed enhancing enzymes and suitable carriers and/or excipients.

In a preferred embodiment, the phytase compositions of the invention additionally comprises an effective amount of one or more feed enhancing enzymes, in particular feed enhancing enzymes selected from the group consisting of α-galactosidases, β-galactosidases, in particular lactases, other phytases, β-glucanases, in particular endo-β-1,4-glucanases and endo-β-1,3(4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phospholipases and cutinases.

The animal feed additive of the invention is supplemented to the mono-gastric animal before or simultaneously with the diet. Preferably, the animal feed additive of the invention is supplemented to the mono-gastric animal simultaneously with the diet. In a more preferred embodiment, the animal feed additive is added to the diet in the form of a granulate or a stabilized liquid.

An effective amount of phytase in food or feed is from about 10–20.000; preferably from about 10 to 15.000, more preferably from about 10 to 10.000, in particular from about 100 to 5.000, especially from about 100 to about 2.000 FYT/kg feed or food.

Examples of other specific uses of the phytase of the invention is in soy processing and in the manufacture of inositol or derivatives thereof.

The invention also relates to a method for reducing phytate levels in animal manure, wherein the animal is fed a feed comprising an effective amount of the phytase of the invention. As stated in the beginning of the present application one important effect thereof is to reduce the phosphate pollution of the environment.

Also within the scope of the invention is the use of a phytase of the invention during the preparation of food or feed preparations or additives, i.e. the phytase excerts its phytase activity during the manufacture only and is not active in the final food or feed product. This aspect is relevant for instance in dough making and baking.

The invention also relates to substantially pure biological cultures of the deposited microorganisms and to strains comprising, as a part of their genetic equipment, a DNA sequence encoding a phytase of the invention. Included within the definition of a substantially pure biological culture is any mutant of said strains having retained the phytase encoding capability.

The invention is described in further detail in the following examples which are not in any way intended to limit the scope of the invention.

EXAMPLES

Materials and Methods

Media:

Phytate replication plates:

Add to 200 ml of melted SC agar 20 ml 20% galactose

800 μl 5% threonine 25 ml solution A 25 ml solution B

200 μl Trace element solution (DSM Catalogue 141)

Solution A:

6 g $CaCl_2$, $2H_2O$ 8 g $MgCl_2$, $6H_2O$ add dd$H_2O$ to 1 l pH=6.5

Solution B:

35.12 g Na-phytate add $H_2O$ to 1 l pH=6.5

Medium A:

| | |
|---|---|
| Yeast Nitrogen Base w/o Amino acids (Difco 0919) | 7.5 g/l |
| Succinic acid (Merck 822260) | 11.3 g/l |
| NaOH (Merck 6498) | 6.8 g/l |
| Casamino acid w/o vitamin (Difco 0288) | 5.6 g/l |
| tryptophan (Merck 8374) | 0.1 g/l |
| Threonine | 1.0 g/l |
| Na-phytate (35.12 g/l pH 6.5) | 125 ml/l |
| Galactose | 20.0 g/l |
| Trace metal (DSM 141) | 1.0 ml/l |
| ad 1 l with $H_2O$ | |

Trace metal solution:

| | |
|---|---|
| Nitrilotriacetic acid | 1.50 g |
| $MgSO_4$,7 $H_2O$ | 3.00 g |
| $MnSO_4$.2$H_2O$ | 0.50 g |
| NaCl | 1.00 g |
| $FeSO_4$, 7$H_2O$ | 0.10 g |
| $CoSO_4$.7$H_2O$ | 0.18 g |
| $CaCl_2$,2$H_2O$ | 0.10 g |
| $ZnSO_4$,7$H_2O$ | 0.18 g |
| $CuSO_4$,5$H_2O$ | 0.01 g |
| $KAl (SO_4)_2$,12$H_2O$ | 0.02 g |
| $H_3BO_3$ | 0.01 g |
| $Na_2MoO_4$.2$H_2O$ | 0.01 g |
| $NiCl_2$,6$H_2O$ | 0.025 g |
| $Na_2Se_3O$,5$H_2O$ | 0.30 g |
| Distilled water | 1 l |
| pH 7.0 | |

First dissolve nitrilotriacetic acid and adjust pH to 6.5 with KOH, then add minerals. Final pH 7.0 (with KOH).

Medium B:

Similar to medium A except for glucose is added as a C-source instead of galactose.

YPD:

10 g yeast extract, 20 g peptone, $H_2O$ to 900 ml. Autoclaved, 100 ml 20% glucose (sterile filtered) added.

YPM:

10 g yeast extract, 20 g peptone, $H_2O$ to 900 ml. Autoclaved, 100 ml 20% maltodextrin (sterile filtered) added.

10×Basal salt:

75 g yeast nitrogen base, 113 g succinic acid, 68 g NaOH, $H_2O$ ad 1000 ml, sterile filtered.

SC-URA:

100 ml 10×Basal salt, 28 ml 20% casamino acids without vitamins, 10 ml 1% tryptophan, H$_2$0 ad 900 ml, autoclaved, 3.6 ml 5% threonine and 100 ml 20% glucose or 20% galactose added.

SC-agar:

SC-URA, 20 g/l agar added.

SC-variant agar:

20 g agar, 20 ml 10×Basal salt, H$_2$O ad 900 ml, autoclaved

General molecular biology methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Unless otherwise specified all enzymes for DNA manipulations, such as e.g. restriction endonucleases, ligases etc., were obtained from New England Biolabs, Inc. The enzymes were used according to the specifications of the suppliers.

Example 1

Cloning and expression of a phytase from *Peniophora lycii* CBS No. 686.96

Deposited organisms:

*Peniophora lycii* CBS No. 686.96 comprises the phytase encoding DNA sequence of the invention.

*Escherichia coli* DSM NO 11312 containing the plasmid comprising the full length cDNA sequence, coding for the phytase of the invention, in the shuttle vector pYES 2.0

Other strains:

Yeast strain: The *Saccharomyces cerevisiae* strain used was W3124 (van den Hazel, H. B; Kielland-Brandt, M. C.; Winther, J. R. in Eur. J. Biochem., 207, 277–283, 1992; (MATa; ura 3-52; leu 2-3, 112; his 3-D200; pep 4-1137; prc1::HIS3; prb1:: LEU2; cir+).

*E. coli* strain: DH10B (Life Technologies)

Plasmids:

The Aspergillus expression vector pHD414 is a derivative of the plasmid p775 (described in EP 238 023). The construction of pHD414 is further described in WO 93/11249.

pYES 2.0 (Invitrogen)

pA2phy2 (See example 1)

Expression cloning in yeast

Expression cloning in yeast was done as described by H. Dalboege et al. (H. Dalboege et al Mol. Gen. Genet (1994) 243:253–260.; WO 93/11249; WO 94/14953), which are hereby incorporated as reference. All individual steps of Extraction of total RNA, cDNA synthesis, Mung bean nuclease treatment, Blunt-ending with T4 DNA polymerase, and Construction of libraries was done according to the references mentioned above.

Fermentation procedure of *Peniophora lycii* CBS No. 686.96 for mRNA isolation:

*Peniophora lycii* CBS 686.96 was inoculated from a plate with outgrown mycelium into a shake flask containing 100 ml medium B (soya 30 g/l, malto dextrin 15 g/l, bacto peptone 5 g/l, pluronic 0.2 g/l) . The culture was incubated stationary at 26° C. for 15 days. The resulting culture broth was filtered through miracloth and the mycelium was frozen down in liquid nitrogen.

mRNA was isolated from mycelium from this culture as described in (H. Dalboege et al Mol. Gen. Genet (1994) 243:253–260.; WO 93/11249; WO 94/14953).

Extraction of total RNA was performed with guanidinium thiocyanate followed by ultracentrifugation through a 5.7 M CsCl cushion, and isolation of poly(A)$^+$RNA was carried out by oligo(dT)-cellulose affinity chromatography using the procedures described in WO 94/14953.

cDNA synthesis:

Double-stranded cDNA was synthesized from 5 mg poly (A)$^+$ RNA by the RNase H method (Gubler and Hoffman (1983) Gene 25:263–269, Sambrook et al. (1989) Molecular cloning: A laboratory manual, Cold Spring Harbor lab., Cold Spring Harbor, N.Y.). The poly(A)$^+$ RNA (5 µg in 5 µl of DEPC-treated water) was heated at 70° C. for 8 min. in a pre-siliconized, RNase-free Eppendorph tube, quenched on ice and combined in a final volume of 50 µl with reverse transcriptase buffer (50 mM Tris-Cl, pH 8.3, 75 mM KCl, 3 mM MgCl$_2$, 10 mM DTT, Bethesda Research Laboratories) containing 1 mM of dATP, dGTP and dTTP and 0.5 mM 5-methyl-dCTP (Pharmacia), 40 units human placental ribonuclease inhibitor (RNasin, Promega), 1.45 µg of oligo(dT)$_{18}$-Not I primer (Pharmacia) and 1000 units SuperScript II RNase H reverse transcriptase (Bethesda Research Laboratories). First-strand cDNA was synthesized by incubating the reaction mixture at 45° C. for 1 hour. After synthesis, the mRNA:cDNA hybrid mixture was gelfiltrated through a MicroSpin S-400 HR (Pharmacia) spin column according to the manufacturer's instructions.

After the gelfiltration, the hybrids were diluted in 250 µl second strand buffer (20 mM Tris-Cl, pH 7.4, 90 mM KCl, 4.6 mM MgCl$_2$, 10 mM (NH$_4$)$_2$SO$_4$, 0.16 mM bNAD+) containing 200 µl of each dNTP, 60 units *E. coli* DNA polymerase I (Pharmacia), 5.25 units RNase H (Promega) and 15 units *E. coli* DNA ligase (Boehringer Mannheim). Second strand cDNA synthesis was performed by incubating the reaction tube at 16° C. for 2 hours and additional 15 min. at 25° C. The reaction was stopped by addition of EDTA to a final concentration of 20 mM followed by phenol and chloroform extractions.

Mung bean nuclease treatment:

The double-stranded cDNA was precipitated at −20° C. for 12 hours by addition of 2 vols 96% EtOH, 0.2 vol 10 M NH$_4$Ac, recovered by centrifugation, washed in 70% EtOH, dried and resuspended in 30 µl Mung bean nuclease buffer (30 mM NaAc, pH 4.6, 300 mM NaCl, 1 mM ZnSO$_4$, 0.35 mM DTT, 2% glycerol) 10 containing 25 units Mung bean nuclease (Pharmacia). The single-stranded hair-pin DNA was clipped by incubating the reaction at 30° C. for 30 min., followed by addition of 70 µl 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-ending with T4 DNA polymerase:

The double-stranded cDNAs were recovered by centrifugation and blunt-ended in 30 ml T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs) by incubating the reaction mixture at 16° C. for 1 hour. The reaction was stopped by addition of EDTA to a final concentration of 20 mM, followed by phenol and chloroform extractions, and precipitation for 12 hours at −20° C. by adding 2 vols 96% EtOH and 0.1 vol 3 M NaAc pH 5.2.

Adaptor ligation, Not I digestion and size selection:

After the fill-in reaction the cDNAs were recovered by centrifugation, washed in 70% EtOH and dried. The cDNA pellet was resuspended in 25 µl ligation buffer (30 mM Tris-Cl, pH 7.8, 10 mM $MgCl_2$, 10 mM DTT, 0.5 mM ATP) containing 2.5 µg non-palindromic BstXI adaptors (Invitrogen) and 30 units T4 ligase (Promega) and incubated at 16° C. for 12 hours. The reaction was stopped by heating at 65° C. for 20 min. and then cooling on ice for 5 min. The adapted cDNA was digested with Not I restriction enzyme by addition of 20 µl water, 5 µl 10× Not I restriction enzyme buffer (New England Biolabs) and 50 units Not I (New England Biolabs), followed by incubation for 2.5 hours at 37° C. The reaction was stopped by heating at 65° C. for 10 min. The cDNAs were size-fractionated by gel electrophoresis on a 0.8% SeaPlaque GTG low melting temperature agarose gel (FMC) in 1×TBE to separate unligated adaptors and small cDNAs. The cDNA was size-selected with a cut-off at 0.7 kb and rescued from the gel by use of b-Agarase (New England Biolabs) according to the manufacturer's instructions and precipitated for 12 hours at −20° C. by adding 2 vols 96% EtOH and 0.1 vol 3 M NaAc pH 5.2.

Construction of libraries:

The directional, size-selected cDNA was recovered by centrifugation, washed in 70% EtOH, dried and resuspended in 30 µl 10 mM Tris-Cl, pH 7.5, 1 mM EDTA. The cDNAs were desalted by gelfiltration through a MicroSpin S-300 HR (Pharmacia) spin column according to the manufacturer's instructions. Three test ligations were carried out in 10 µl ligation buffer (30 mM Tris-Cl, pH 7.8, 10 mM $MgCl_2$, 10 mM DTT, 0.5 mM ATP) containing 5 µl double-stranded cDNA (reaction 20 tubes #1 and #2), 15 units T4 ligase (Promega) and 30 ng (tube #1), 40 ng (tube #2) and 40 ng (tube #3, the vector background control) of BstXI-NotI cleaved pYES 2.0 vector. The ligation reactions were performed by incubation at 16° C. for 12 hours, heating at 70° C. for 20 min. and addition of 10 µl water to each tube. 1 µl of each ligation mixture was electroporated into 40 µl electrocompetent *E. coli* DH10B cells (Bethesda research Laboratories) as described (Sambrook et al. (1989) Molecular cloning: A laboratory manual, Cold Spring Harbor lab., Cold Spring Harbor, N.Y.). Using the optimal conditions a library was established in *E. coli* consisting of pools. Each pool was made by spreading transformed *E. coli* on LB+ampicillin agar plates giving 15.000–30.000 colonies/plate after incubation at 37° C. for 24 hours. 20 ml LB+ampicillin was added to the plate and the cells were suspended herein. The cell suspension was shaked in a 50 ml tube for 1 hour at 37° C. Plasmid DNA was isolated from the cells according to the manufacturer's instructions using QIAGEN plasmid kit and stored at −20° C.

1 µl aliquots of purified plasmid DNA (100 ng/ml) from individual pools were transformed into *S. cerevisiae* W3124 by electroporation (Becker and Guarante (1991) Methods Enzymol. 194:182–187) and the transformants were plated on SC agar containing 2% glucose and incubated at 30° C.

Identification of positive colonies:

After 3–5 days of growth, the agar plates were replica plated onto a set of the phytate replication plates, and incubated for 3–5 days at 30° C. 1% LSB-agarose containing 0.2M CaCl2 is poured over the plates and after 1–4 days the phytase positive colonies are identified as colonies surrounded by a clearing zone.

Cells from enzyme-positive colonies were spread for single colony isolation on agar, and an enzyme-producing single colony was selected for each of the phytase-producing colonies identified.

Isolation of a cDNA gene for expression in Aspergillus:

A phytase-producing yeast colony was inoculated into 20 ml YPD broth in a 50 ml glass test tube. The tube was shaken for 2 days at 30° C. The cells were harvested by centrifugation for 10 min. at 3000 rpm.

DNA was isolated according to WO 94/14953 and dissolved in 50 ml water. The DNA was transformed into *E. coli* by standard procedures. Plasmid DNA was isolated from *E. coli* using standard procedures, and analyzed by restriction enzyme analysis.

The cDNA insert was excised using the restriction enzymes Hind III and Xba I and ligated into the Aspergillus expression vector pHD414 resulting in the plasmid pA2phy2.

The cDNA inset of Qiagen purified plasmid DNA of pA2phy2 (Qiagen, USA) was sequenced with the Taq deoxy terminal cycle sequencing kit (Perkin Elmer, USA) and synthetic oligonucleotide primers using an Applied Biosystems ABI PRISM™ 377 DNA Sequencer according to the manufacturers instructions.

Transformation of *Aspergillus oryzae* or *Aspergillus niger*

Protoplasts are prepared as described in WO 95/02043, p. 16, line 21—page 17, line 12, which is hereby incorporated by reference.

100 µl of protoplast suspension is mixed with 5–25 µg of the appropriate DNA in 10 µl of STC (1.2 M sorbitol, 10 mM Tris-HCl, pH=7.5, 10 mM $CaCl_2$). Protoplasts are mixed with p3SR2 (an *A. nidulans* amdS gene carrying plasmid) (Tove Christensen et al. Bio/Technology, pp 1419–1422 vol.6, December 1988). The mixture is left at room temperature for 25 minutes. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates (Cove, Biochem. Biophys. Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* transformants

Each of the *A. oryzae* transformants are inoculated in 10 ml of YPM (cf. below) and propagated. After 2–5 days of incubation at 30° C., the supernatant is removed.

The phytase activity is identified by applying 20 µl supernatant to 4 mm diameter holes punched out in 1% LSB-agarose plates containing 0.1M Sodiumacetate pH 4.5 and 0.1% Inositol hexaphosphoric acid. The plates are left over night at 37° C. A buffer consisting of 0.1M CaCl2 and 0.2M Sodium acetate pH 4.5 is poured over the plates and the plates are left at room temperature for 1 h. Phytase activity is then identified as a clear zone.

Fed batch fermentation:

Fed batch fermentation was performed in a medium comprising maltodextrin as a carbon source, urea as a nitrogen source and yeast extract. The fed batch fermentation was performed by inoculating a shake flask culture of *A. oryzae* host cells in question into a medium comprising 3.5% of the carbon source and 0.5% of the nitrogen source. After 24 hours of cultivation at pH 7.0 and 34° C. the continuous supply of additional carbon and nitrogen sources were initiated. The carbon source was kept as the limiting factor and it was secured that oxygen was present in excess. The fed batch cultivation was continued for 4 days.

Isolation of the DNA sequence shown in SEQ ID No. 1:

The phytase encoding part of the DNA sequence shown in SEQ ID No. 1 coding for the phytase of the invention can be obtained from the deposited organism Escherichia coli DSM 11312 by extraction of plasmid DNA by methods known in the art (Sambrook et al. (1989) Molecular cloning: A laboratory manual, Cold Spring Harbor lab., Cold Spring Harbor, N.Y.).

Cloning and expression was done by using the Expression cloning in yeast technique as described above.

mRNA was isolated from *Peniophora lycii*, CBS No. 686.96, grown as described above.

Mycelia were harvested after 15 days' growth, immediately frozen in liquid nitrogen and stored at −80° C. A library from Peniophora lycii, CBS No. 686.96, consisting of approx. 9×10$^5$ individual clones was constructed in *E. coli* as described with a vector background of 1%. Plasmid DNA from some of the pools was transformed into yeast, and 50–100 plates containing 250–400 yeast colonies were obtained from each pool.

Phytase-positive colonies were identified and isolated as described above and inoculated into 20 ml YPD broth in a 50 ml glass test tube. The tube was shaken for 2 days at 30° C. The cells were harvested by centrifugation for 10 min. at 3000 rpm. DNA was isolated according to WO 94/14953 and dissolved in 50 µl water. The DNA was transformed into *E. coli* by standard procedures. Plasmid DNA was isolated from *E. coli* using standard procedures, and the DNA sequence of the cDNA encoding the phytase was sequenced with the Taq deoxy terminal cycle sequencing kit (Perkin Elmer, USA) and synthetic oligonucleotide primers using an Applied Biosystems ABI PRISM™ 377 DNA Sequencer according to the manufacturers instructions. The DNA sequence of the cDNA encoding the phytase is shown in SEQ ID No. 1 and the corresponding amino acid sequence is shown in SEQ ID No. 2. In SEQ ID No. 1 DNA nucleotides from No 1 to No. 1320 define a phytase encoding region.

The part of the DNA sequence in SEQ ID NO 1, which is encoding the mature part of the phytase is position 91 to 1320, which corresponds to amino acid position 31–439 in SEQ ID NO 2.

The cDNA is obtainable from the plasmid in DSM 11312.

Total DNA was isolated from a yeast colony and plasmid DNA was rescued by transformation of *E. coli* as described above. In order to express the phytase in Aspergillus, the DNA was digested with appropriate restriction enzymes, size fractionated on gel, and a fragment corresponding to the phytase gene was purified. The gene was subsequently ligated to pHD414, digested with appropriate restriction enzymes, resulting in the plasmid pA2phy2.

After amplification of the DNA in *E. coli* the plasmid was transformed into *Aspergillus oryzae* as described above.

Test of *A. oryzae* transformants

Each of the transformants were tested for enzyme activity as described above. Some of the transformants had phytase activity which was significantly larger than the *Aspergillus oryzae* background. This demonstrates efficient expression of the phytase in *Aspergillus oryzae*.

Example 2

Purification and characterization of the phytase from Peniophora lycii expressed in *Aspergillus oryzae*

The Peniophora lycii phytase was expressed in and excreted from *Aspergillus oryzae* IFO 4177.

Filter aid was added to the culture broth which was filtered through a filtration cloth. This solution was further filtered through a Seitz depth filter plate resulting in a clear solution. The filtrate was concentrated by ultrafiltration on 3 kDa cut-off polyethersulphone membranes followed by diafiltration with distilled water to reduce the conductivity. The pH of the concentrated enzyme was adjusted to pH 7.5. The conductivity of the concentrated enzyme was 1.2 mS/cm.

The phytase was applied to a Q-sepharose FF column equilibrated in 20 mM Tris/CH$_3$COOH, pH 7.5 and the enzyme was eluted with an increasing linear NaCl gradient (0→0.5M). The phytase activity eluted as a single peak. This peak was pooled and (NH$_4$)$_2$SO$_4$ was added to 1.5M final concentration. A Phenyl Toyopearl 650S column was equilibrated in 1.5M (NH$_4$)$_2$SO$_4$, 10 mM succinic acid/NaOH, pH 6.0 and the phytase was applied to this column and eluted with a decreasing linear (NH$_4$)$_2$SO$_4$ gradient (1.5→0M). Phytase containing fractions were pooled and the buffer was exchanged for 20 mM Tris/CH$_3$COOH, pH 7.5 on a Sephadex G25 column. The G25 filtrate was applied to a Q-sepharose FF column equilibrated in 20 mM Tris/CH$_3$COOH, pH 7.5. After washing the column extensively with the equilibration buffer, the phytase was eluted with an increasing linear NaCl gradient (0→0.5M). The phytase activity was pooled and the buffer was exchanged for 20 mM Tris/CH$_3$COOH, pH 7.5 by dialysis. The dialysed phytase was applied to a SOURCE 30Q column equilibrated in 20 mM Tris/CH$_3$COOH, pH 7.5. After washing the column thoroughly with the equilibration buffer a phytase was eluted with an increasing linear NaCl gradient (0→0.3M). Fractions from the SOURCE 30Q column were analyzed by SDS-PAGE and pure phytase fractions were pooled.

The *Peniophora phytase* migrates in the gel as a band with $M_r$=67 kDa. N-terminal amino acid sequencing of the 67 kDa component was carried out following SDS-PAGE and electroblotting onto a PVDF-membrane. The following N-terminal amino acid sequence could be deduced:

Leu-Pro-Ile-Pro-Ala-Gln-Asn-SEQ ID NO:3

The sequence corresponds to amino acid residues 31–37 in the cDNA derived amino acid sequence.

Accordingly a mature amino acid sequence of the phytase when expressed in Aspergillus is supposed to be no. 31–439 of SEQ ID no 2.

Example 3

Characterization of the phytase of *Peniophora lycii*, as present in the supernatant of crude fermentation broth The characterization below was performed on the supernatant of crude culture broth.

Phytase activity assay:

For each phytase sample two aliquots of 20 µl are added to 100 µl phytic acid (5 mM sodium phytate in 0.1 M sodium acetate buffer pH 5.5).

At time T=0 minutes 100 µl of Fe-reagent (1.1 g FeSO$_4$, 7 H$_2$O in 15 ml ammonium molybdate solution (2.5 g (NH$_4$)$_6$Mo$_7$O$_{24}$,4 H$_2$O and 8 ml H$_2$SO$_4$ diluted to 250 ml with water)) is added to the reference sample. The reference mixture is incubated for 5 minutes at 37° C. The intensity of the blue colour is measured spectrophotometrically at 750 nm.

The enzyme sample is incubated for 30 minutes at 37° C. At T=30 minutes 100 µl of Fe-reagent is added. The samples incubate for 5 minutes at 37° C. and is measured spetrophotometrically at 750 nm. The difference between the enzyme sample and the reference sample is indicative of the quantity of phosphate released in relation to a calibration curve of phosphate.

Temperature stability

The stability of phytase was measured by pre-incubating the enzyme samples for 20 minutes at the temperatures indicated in the table below followed by cooling the samples to room temperature prior to measuring the residual activity.

The results obtained are also shown in the table below, viz. relative to the residual activity following incubation 20 minutes at 26° C.

|  | Residual activity | | |
| --- | --- | --- | --- |
| Strain | 26° C. | 60° C. | 70° C. |
| Peniophora lycii | 100 | 82 | 82 | pH-optimum

The pH profile was also determined on the supernatant of crude culture broth and using the phytase activity assay described above. The 5 mM phytic acid solution was made in the following buffers: pH 3.0 (0.1 M glycine/HCl), pH 4.0 (0.1 M sodium acetate), pH 5.0 (sodium acetate), pH 5.5 (sodium acetate), pH 6.0 (50 mM MES), pH 7.0 (0.1 M Tris-HCl), pH 8.0 (0.1 M Tris-HCl), pH 9.0 (0.1 M glycine/NaOH).

The results are shown in the table below, in relative values, index 100 indicating the activity at pH 5.0.

| Strain | pH 3.0 | pH 4.0 | pH 5.0 | pH 5.5 | pH 6.0 | pH 7.0 | pH 8.0 | pH 9.0 |
| --- | --- | --- | --- | --- | --- | --- | --- | --- |
| P. lycii | 31 | 68 | 100 | 68 | 25 | 20 | 11 | 2 |

Example 4

Characterization of the purified phytase of Peniophora lycii

The phytase of Peniophora lycii was expressed in Aspergillus and purified as described in Example 2.

The phytase activity is measured using the following assay: 10 μl diluted enzyme samples (diluted in 0.1 M sodium acetate, 0.01% Tween20, pH 5.5) were added into 250 μl 5 mM sodium phytate (Sigma) in 0.1 M sodium acetate, 0.01% Tween20, pH 5.5 (pH adjusted after dissolving the sodium phytate; the is substrate was preheated) and incubated for 30 minutes at 37° C. The reaction was stopped by adding 250 p1 10 % TCA and free phosphate was measured by adding 500 μl 7.3 g $FeSO_4$ in 100 ml molybdate reagent (2.5 g $(NH_4)_6Mo_7O_{24}.4H_2O$ in 8 ml $H_2SO_4$ diluted to 250 ml). The absorbance at 750 nm was measured on 200 μl samples in 96 well microtiter plates. Substrate and enzyme blanks were included. A phosphate standard curve was also included (0–2 mM phosphate). 1 FYT equals the amount of enzyme that releases 1 μmol phosphate/min at the given conditions.

Temperature profiles were obtained by running the assay at various temperatures (preheating the substrate).

Temperature stability was investigated by preincubating the phytases in 0.1 M sodium phosphate, pH 5.5 at various temperatures before measuring the residual activity.

The pH-stability was measured by incubating the enzyme at pH 3 (25 mM glycine-HCl), pH 4-5 (25 mM sodium acetate), pH 6 (25 mM MES), pH 7–9 (25 mM Tris-HCl) for 1 hour at 40 ° C., before measuring the residual activity.

The pH-profiles were obtained by running the assay at the various pH using the same buffer-systems (50 mM, pH was re-adjusted when dissolving the substrate).

The results of the above pH-profile, pH-stability, temperature-profile and temperature stability studies are shown in FIG. 1, 2, 3 and 4, respectively.

From FIG. 1 it appears that the phytase of Peniophora lycii has a reasonable activity at pH 3–6 (i.e. more than 40% of the maximum activity). At pH 3.5–5.5 more than 60% of the maximum activity is found, at pH 3.8–5.0 more than 90%. Optimum pH seems to be in the area of pH 4–5.

Figure 2:
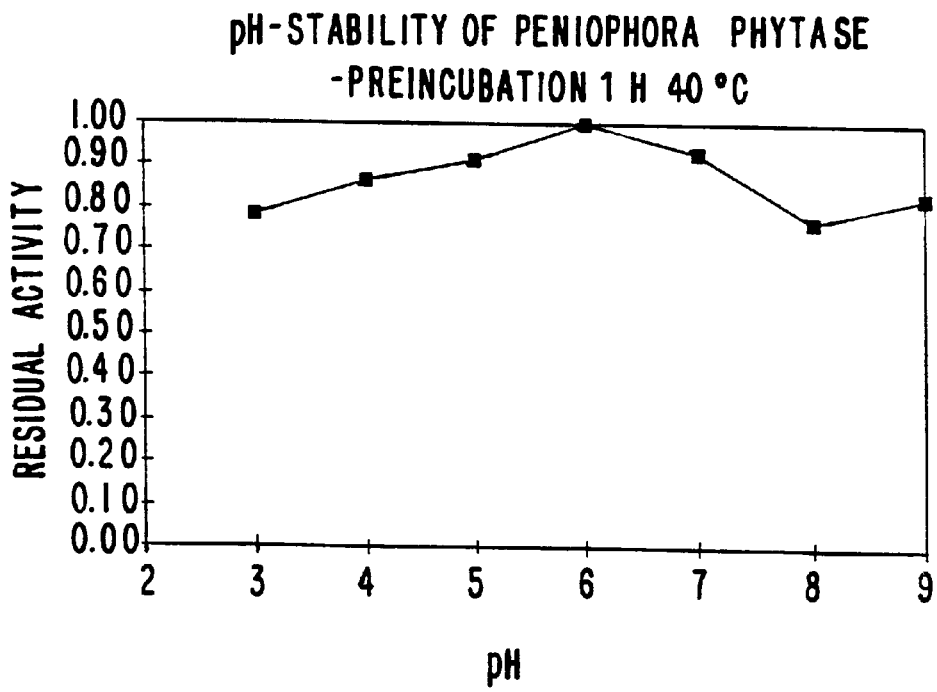
FIG. 2 a pH-stability curve thereof (pre-incubation 1 h 40° C.)

It is apparent from FIG. 2 that the phytase of Peniophora lycii is very stable (i.e. more than 80% of the maximum activity retained) for 1 hour at 40° C. in the whole range of pH 3–9.

Figure 3:
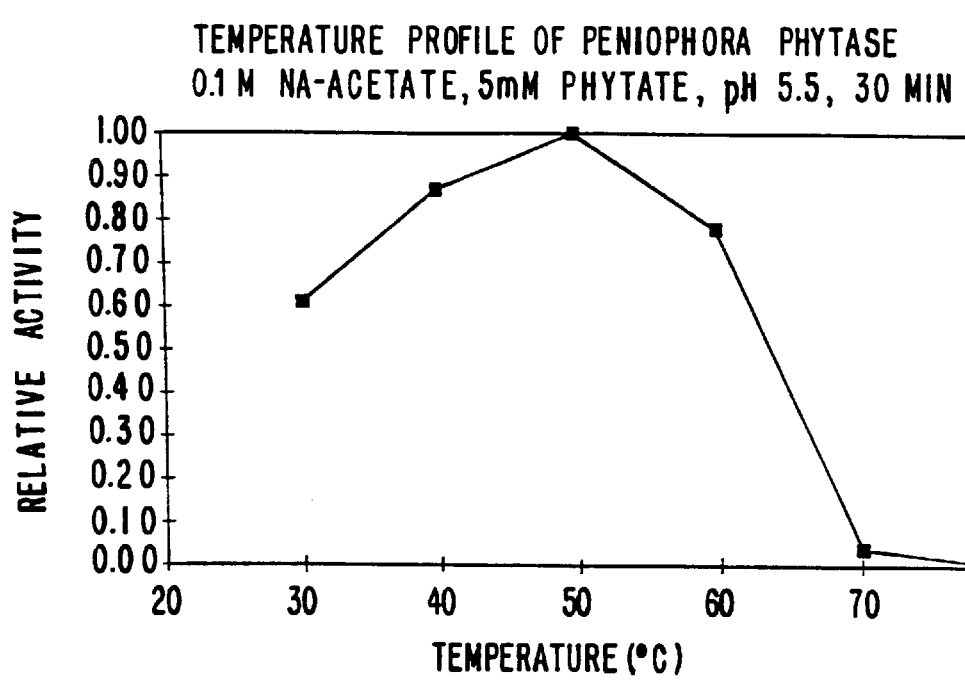
FIG. 3 a temperature-activity curve thereof (0.1M Na-acetate, 5 mM phytate, pH 5.5, 30 min.), FIG. 4 a temperature-stability curve thereof (pre-incubation 60 min. in 0.1M Na-acetate pH 5.5), FIG. 5 a Differential Scanning Calorimetry (DSC) curve thereof (0.1M Na-acetate, pH 5.5; $T_d$=59.6° C.), FIGS. 6–7 NMR spectra, stacked plots (up to 24 h), showing the product profiling of an *Aspergillus niger* and the *Peniophora phytase*, respectively, FIGS. 8–9 NMR spectra as above, but stacked plots up to 4.5 h, FIGS. 10a–c NMR profiles observed after 20 minutes (at pH 5.5), 24 hours (at pH 5.5) and 20 minutes (at pH 3.5), respectively, FIG. 11 curves showing concentration versus time of Ins(1,2)P2 and Ins(2)P, respectively, and FIG. 12–13 curves showing the release of inorganic phosphate versus time from corn at pH 5.5 and pH 3.5, respectively.

As regards the temperature profile, it is apparent from FIG. 3, that the Peniophora lycii phytase has a reasonable activity at temperatures of 30–65° C. (i.e. more than 60% of the maximum activity), whereas at temperatures of 35–62° C. the activity is more than 70% of the maximum activity, and the optimum temperature could be close to 50° C.

Figure 4:
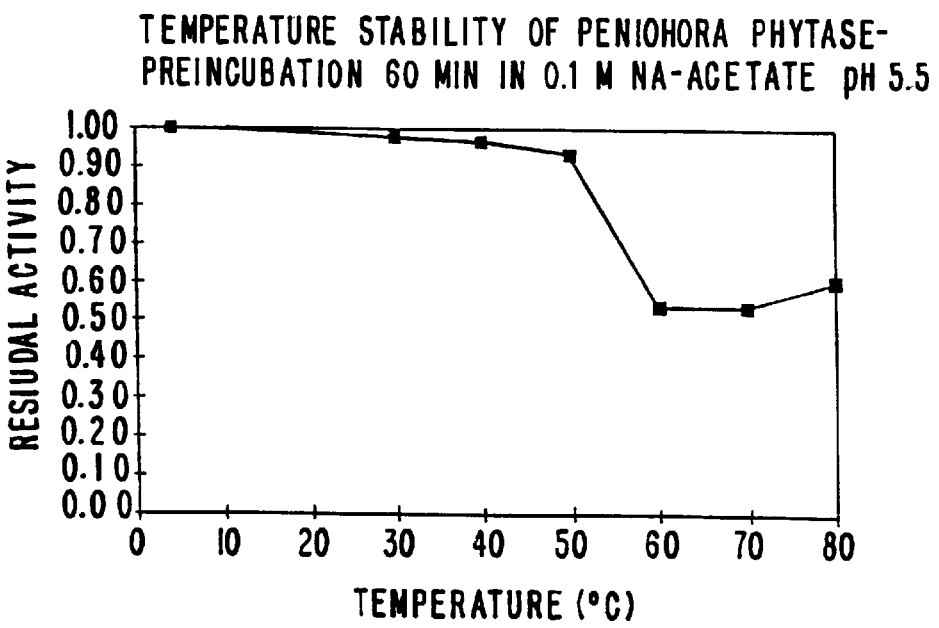

And finally, as regards the temperature stability results shown at FIG. 4, the phytase of the invention is very stable at temperatures of 0 to about 50° C. (i.e. more than 90% residual activity). A certain decline in residual activity is seen after preincubation at temperatures above 50° C. Anyhow, at 60–80° C. some 50–60% of the residual activity still remains.

This fact is contemplated to be due to the enzyme being surprisingly capable of refolding following its thermal denaturation. The degree of refolding will depend on the exact conditions (pH, enzyme concentration).

Figure 5:
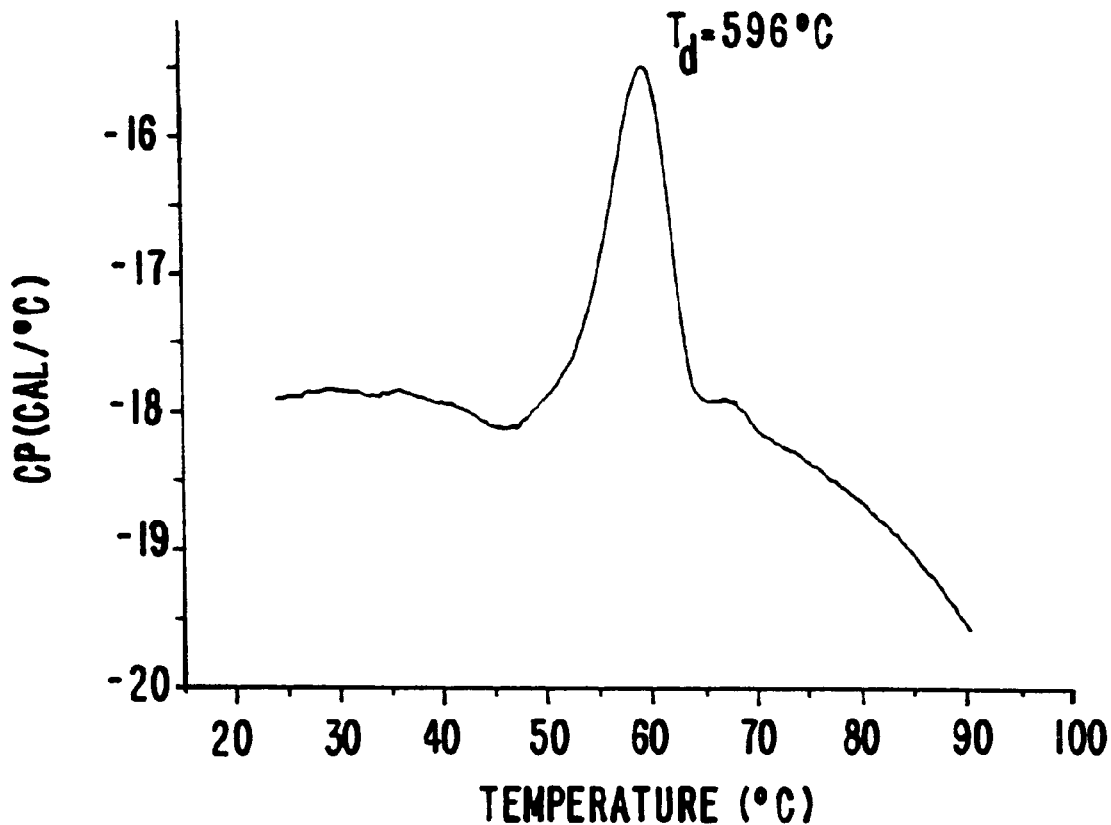

FIG. 5 shows the result of differential scanning calorimetry (DSC) measurements on the Peniophora phytase.

In DSC the heat consumed to keep a constant temperature increase in the sample-cell is measured relative to a reference cell. A constant heating rate is kept (e.g. 90° C./hour). An endothermal process (heat consuming process—e.g. the unfolding of an enzyme/protein) is observed as an increase in the heat transferred to the cell in order to keep the constant temperature increase.

DSC was performed using the MC2-apparatus from MicroCal. Cells were equilibrated 20 minutes at 20° C. before scanning to 90° C. at a scan rate of 90°/h. Samples of around 2.5 mg/ml Peniophora phytase in 0.1 M sodium acetate, pH 5.5 were loaded.

The temperature stability studies were confirmed by DSC, since from FIG. 5 it is apparent that the Peniophora phytase has a denaturation or "melting" temperature of about 60° C. at pH 5.5.

Example 4a

Determination of the specific activity of the Peniophora phytase

The specific activity is determined on a highly purified sample of the phytase (the purity was checked beforehand on an SDS poly acryl amide gel showing the presence of only one component).

The protein concentration in the phytase sample was determined by amino acid analysis as follows: An aliquot of the phytase sample was hydrolyzed in 6N HCl, 0.1% phenol for 16 h at 110 C in an evacuated glass tube. The resulting amino acids were quantified using an Applied Biosystems 420A amino acid analysis system operated according to the manufacturers instructions. From the amounts of the amino acids the total mass—and thus also the concentration—of protein in the hydrolyzed aliquot can be calculated.

The activity is determined in the units of FYT. One FYT equals the amount of enzyme that liberates 1 micromol inorganic phosphate from phytate (5 mM phytate) per minute at pH 5.5, 37 C; assay described e.g. in example 4.

The specific activity is calculated to 987 FYT/mg enzyme protein.

Example 5

Time-resolved product-profiling of phytase-catalyzed hydrolysis of phytic acid by $^1$H NMR spectroscopy The hydrolysis of phytic acid (PA) catalyzed by the Peniophora phytase and by a commercial *Aspergillus niger* phytase (Phytase Novo®) was investigated (27 mM phytate, 1 FYT/ml, pH 5.5 and 3.5, and 27° C.) by $^1$H NMR profiling the product mixture in the course of 24 hours.

In the following (Ins(p,q,r, . . . )$P_n$ denotes myo-inositol carrying in total n phosphate groups attached to positions p, q, r, . . . For convenience Ins(1,2,3,4,5,6)$P_6$ (phytic acid) is abbreviated PA. Please refer, however, to the section "Nomenclature and position specificity of phytases" in the general part of this application.

The technique provide specific information about initial points of attack by the enzyme on the PA molecule, as well as information about the identity of the end product. On the other side the evolving patterns of peaks reflecting the composition of the intermediate product mixtures, provide a qualitative measure, a finger print, suitable for identification of similarities and differences between individual enzymes.

NMR, like most other analytical methods, can distinguish between stereo-isomers which are not mirror images (diastereomers), but not between a set of isomers, which are mirror-images (enantiomers), since they exhibit identical NMR spectra.

Thus, Ins(1,2,4,5,6) $P_5$ (3-phosphate removed) exhibits a NMR spectrum different from Ins(1,2,3,4,5)$P_5$ (6-phosphate removed) because the isomers are diastereomers.

However, the NMR spectra of Ins(1,2,4,5,6)$P_5$ and Ins(2, 3,4,5,6)$P_5$ (1-phosphate removed) are identical because the isomers are enantiomers. The same holds for the pair Ins(1, 2,3,4,5)$P_5$ and Ins(1,2,3,5,6)$P_5$ (4-phosphate removed).

Thus, by NMR it is not possible to distinguish between a 3- and a 1-phytase, and it is not possible to distinguish between a 6- and a 4-phytase (or a L-6 and a D-6-phytase using the lowest-locant-rule).

Biased by the description of 3- and 6-phytases in the literature, we have used the terms 3- and 6-phytases for our enzymes, but, though unlikely, we do not actually know if we have a 1- and a 4-phytase instead.

Experimental

NMR spectra were recorded at 300K (27° C.) on a Bruker DRX400 instrument equipped with a 5 mm selective inverse probe head. 16 scans preceded by 4 dummy scans were accumulated using a sweep width of 2003 Hz (5 ppm) covered by 8K data points. Attenuation of the residual HOD resonance was achieved by a 3 seconds presaturation period. The spectra were referenced to the HOD signal ($\delta$4.70).

PA samples for NMR analysis were prepared as follows: PA (100 mg, Phytic acid dipotassium salt, Sigma P-5681) was dissolved in deionized water (4.0 ml) and pH adjusted to 5.5 or 3.5 by addition of aqueous NaOH (4 N). Deionized water was added (ad 5 ml) and 1 ml portions, each corresponding to 20 mg of phytic acid, were transferred to screw-cap vials and the solvent evaporated (vacuum centrifuge). The dry samples were dissolved in deuterium oxide (2 ml, Merck 99.5% D) and again evaporated to dryness (stored at –18° C. until use).

For NMR analysis one 20 mg phytic acid sample was dissolved in deuterium oxide (1.0 ml, Merck 99.95% D). The solution was transferred to a NMR tube and the H NMR spectrum recorded. Enzyme solution (1 FTU, dissolved in/diluted, as appropriate, with deuterium oxide) was added followed by thorough mixing (1 minute). $^1$H NMR spectra were recorded immediately after addition of enzyme (t=0), then after 5, 10, 15, 20, 25, 30, 45, 60, 75, 90, 105, 120, 135 150, 165, 180, 195, 210 minutes (=3.5 hours), 4.5, 5.5 6.5, 7.5, 8.5, 9.5, 11.5, 13.5, 15.5, 17.5, 19.5, 21.5, and 23.5 hours. The pH in the NMR tube was measured. Additional spectra were acquired after 48 and 120 hours (5 days), where a portion of substrate (PA, 6 mg) was added to probe if the enzyme retained its catalytic activity.

By means of 2D NMR analysis of inositol phosphate mixtures obtained by partial digestion of PA, in conjunction with published NMR data (Scholz, P.; Bergmann, G., and Mayr, G. W.: Methods in Inositide Research (Ed. Irvine, R. F.), pp. 65–82, Raven Press, Ltd., New York (1990)), characteristic $^1$H NMR signals attributable to Ins(1,2,3,4,5,6)$P_6$ (PA), Ins(1,2,4,5,6) $P_5$, Ins(1,2,3,4,5)$P_5$, Ins(1,2,5,6) $P_4$, Ins(1,2,6)$P_3$, Ins(1,2)$P_2$, and Ins(2)P, were identified and permitted relative quantification of these species during the course of the reaction.

Figure 6:
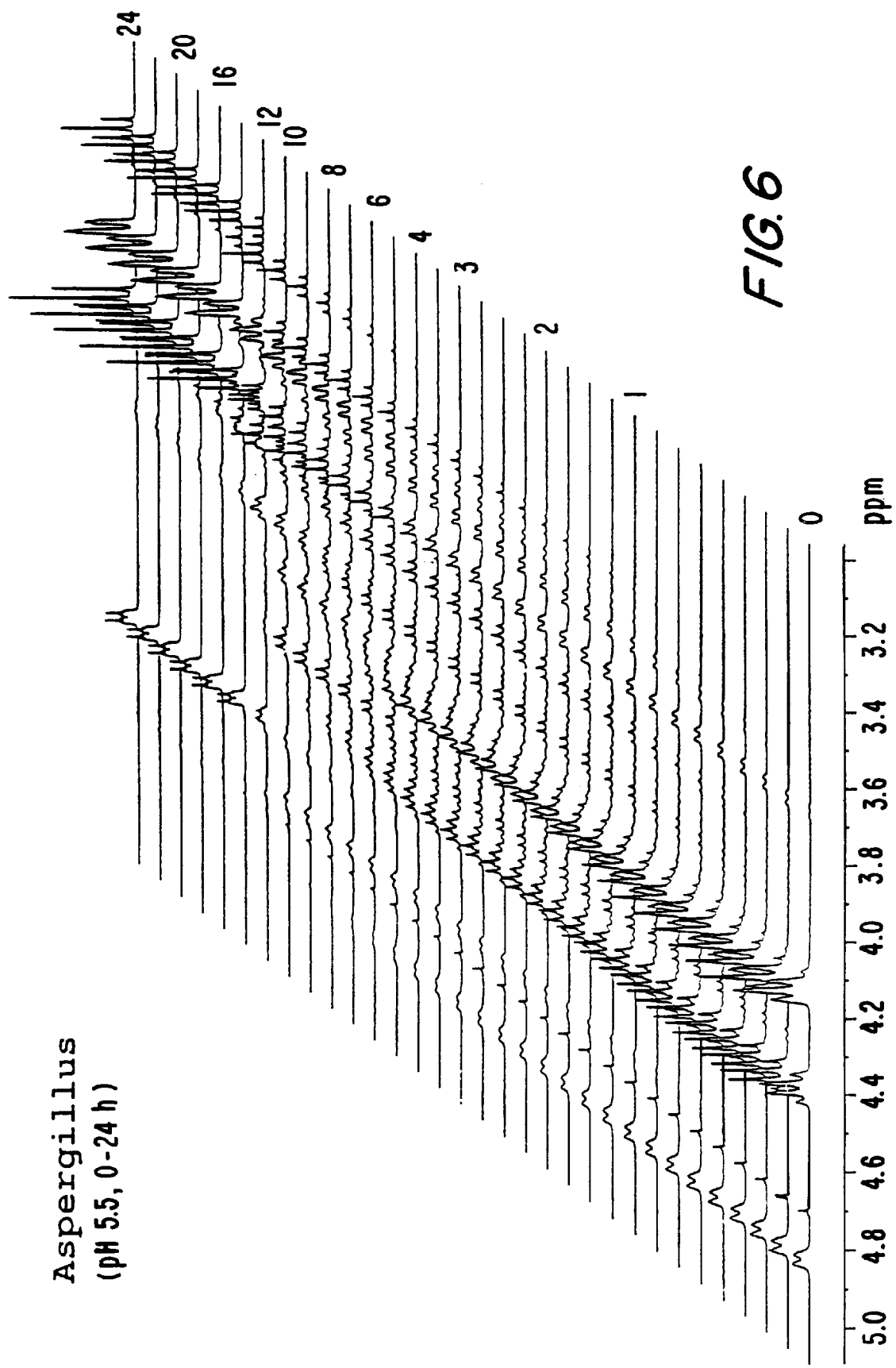
Figure 7:
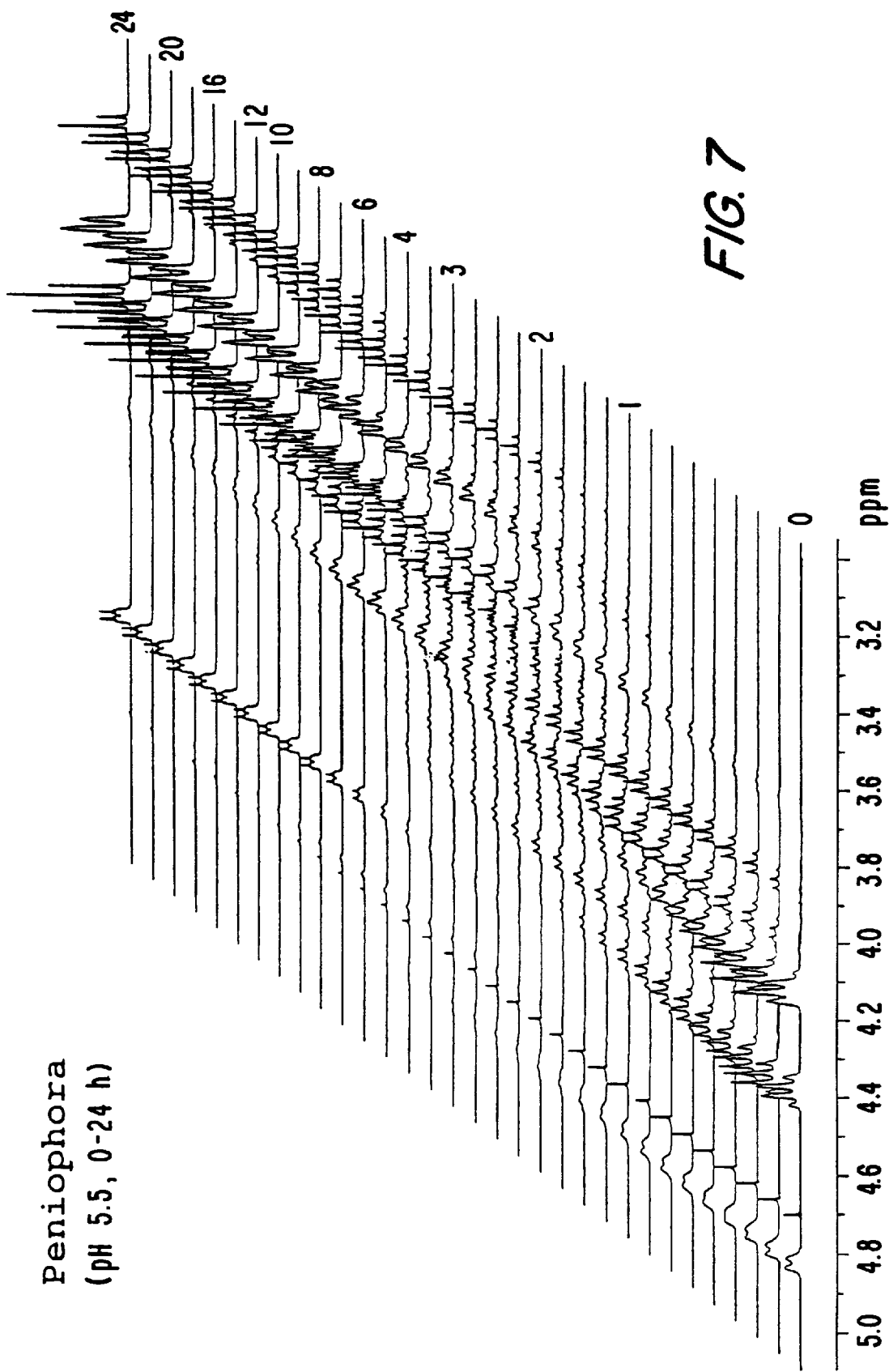

Stacked plots of product profiles for the Aspergillus phytase and the Peniophora phytase covering 24 hours of reaction time at pH 5.5 is presented in FIG. 6 and FIG. 7, respectively.

The signal at $\delta$3.25(t) represents H-5 in Ins(1,2)$P_2$ whereas the signal at $\delta$3.18(t) represents H-5 in Ins(2)P. Ins(1,2)$P_2$ starts accumulating after about 4 hours of reaction time with the *Aspergillus phytase* and after about 1 hours of reaction time with the Peniophora phytase. Ins(2)P is observed after about 10 hours of reaction with the *Aspergillus phytase* and after about 3 hours of reaction with the Peniophora phytase. After 24 hours of reaction the amount or level of Ins(1,2)$P_2$ is very low for both phytases, whereas the amount of Ins(2)P is maximum for both phytases after 24 hours.

Accordingly, the profiles observed after 24 hours of reaction time demonstrate that both phytases degrade PA to Ins(2)P.

For both enzymes the reaction mixture at 24 h comprised in addition to Ins(2)P minor amounts of Ins(1,2)$P_2$. Prolonged reaction times (several days) resulted in disappearance of the residual Ins(1,2)$P_2$, but the fully dephosphorylated species, inositol (Ins), was not observed at all. The observation is not explained by irreversible inhibition/denaturation of the enzyme, since the enzymes retained their catalytic activities for prolonged periods, as demonstrated by their ability to digest fresh portions of PA added to the NMR tubes after keeping them 5 days at room temperature.

Figure 8:
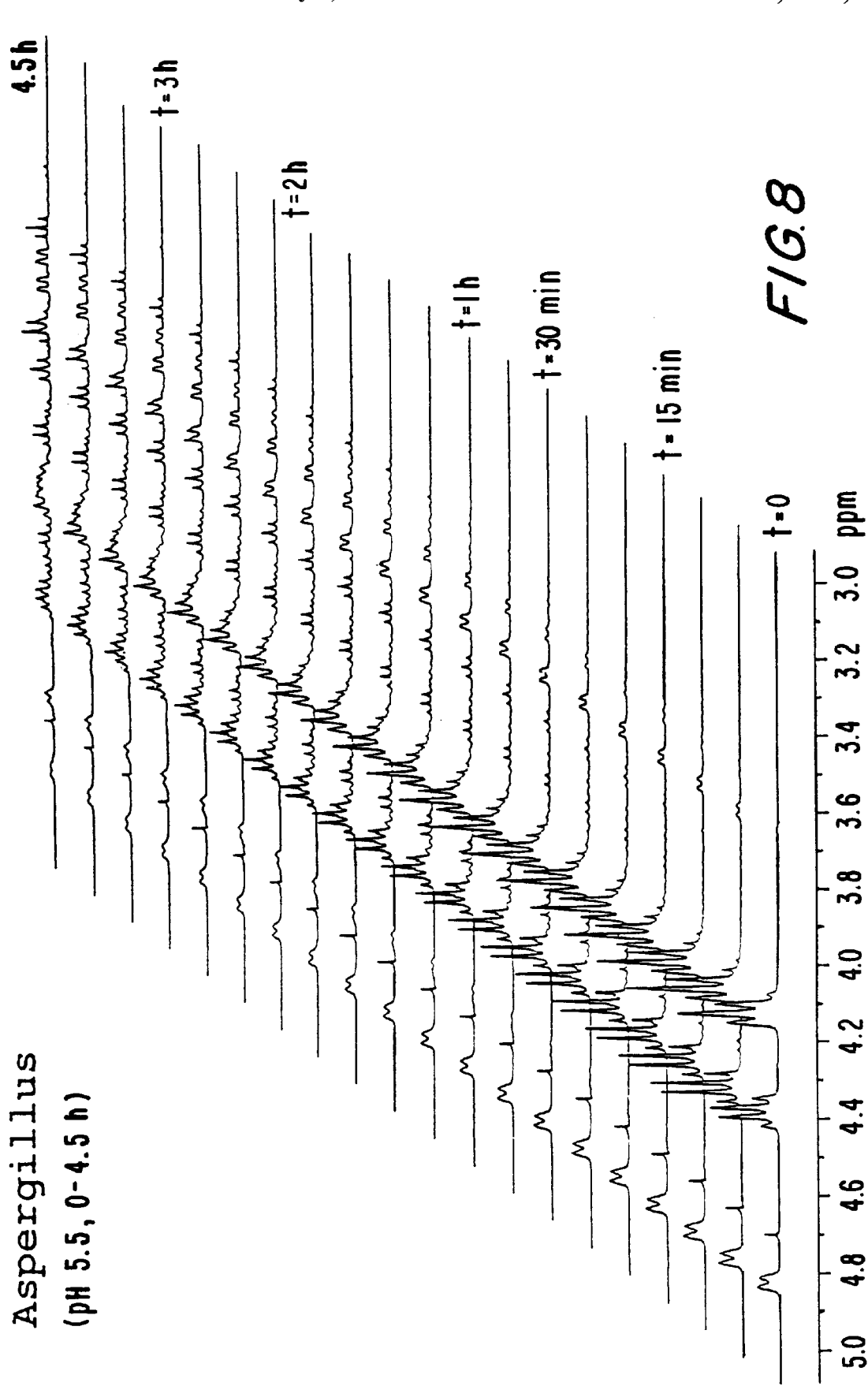
Figure 9:
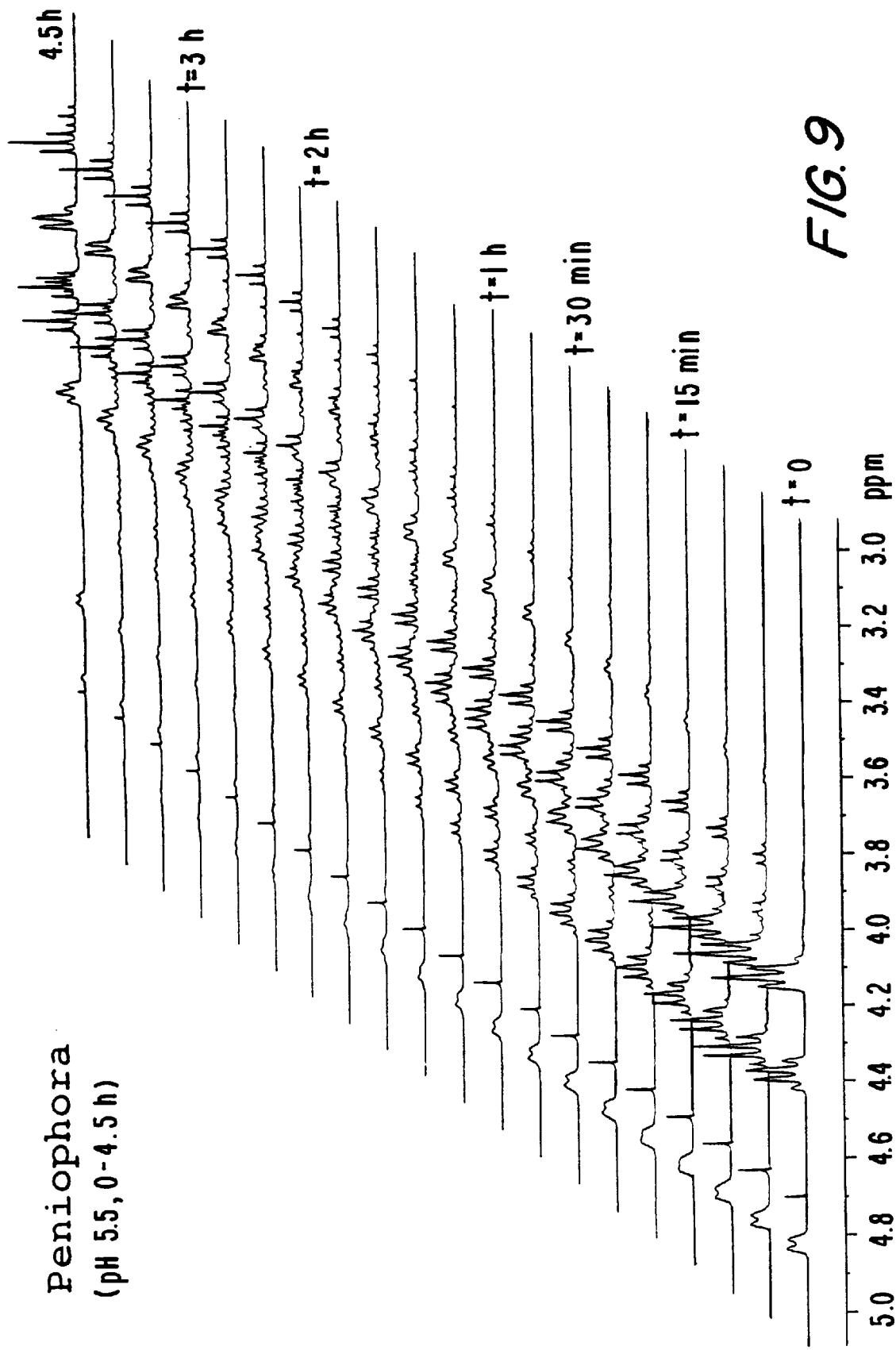

Turning now to FIGS. 8 and 9, these depict in more detail the profiles evolving at pH 5.5 during the initial 4.5 hours. It is inferred from FIG. 10 that H-3 in Ins(1,2,4,5,6)$P_5$ (designated A) shows a signal at $\delta$3.66(dd), H-6 in Ins(1,2, 3,4,5)$P_5$ (B) a signal at $\delta 3.87(t)$ and H-3 in 25 Ins(1,2,5,6)$P_4$ (C) a signal at $\delta 3.56(dd)$. Now, compound A corresponds to phosphate in position 3 having been hydrolyzed, B position 6 and C position 3 and 4.

It is apparent from FIG. 8 that compound A appears as the major primary product (t=5 min) using the *Aspergillus phytase*, whereas compound B does not appear. Compound C appears after 20–25 minutes.

From FIG. 9 (the *Peniophora phytase*) one infers that compound B appears as the major primary product (t=5min) using the *Peniophora phytase*.

The signals at $\delta 4.82(dt, H-2)$, 4.38 (q, H-4/H-6), 4.13(q, H- 5) and 4.11(dt,H1/H3) are attributable to the substrate, phytic acid, PA. Comparing FIGS. 8 and 9 it is apparent, that these peaks diminish faster with the *Peniophora phytase* than with the *Aspergillus phytase*.

Figure 10A:
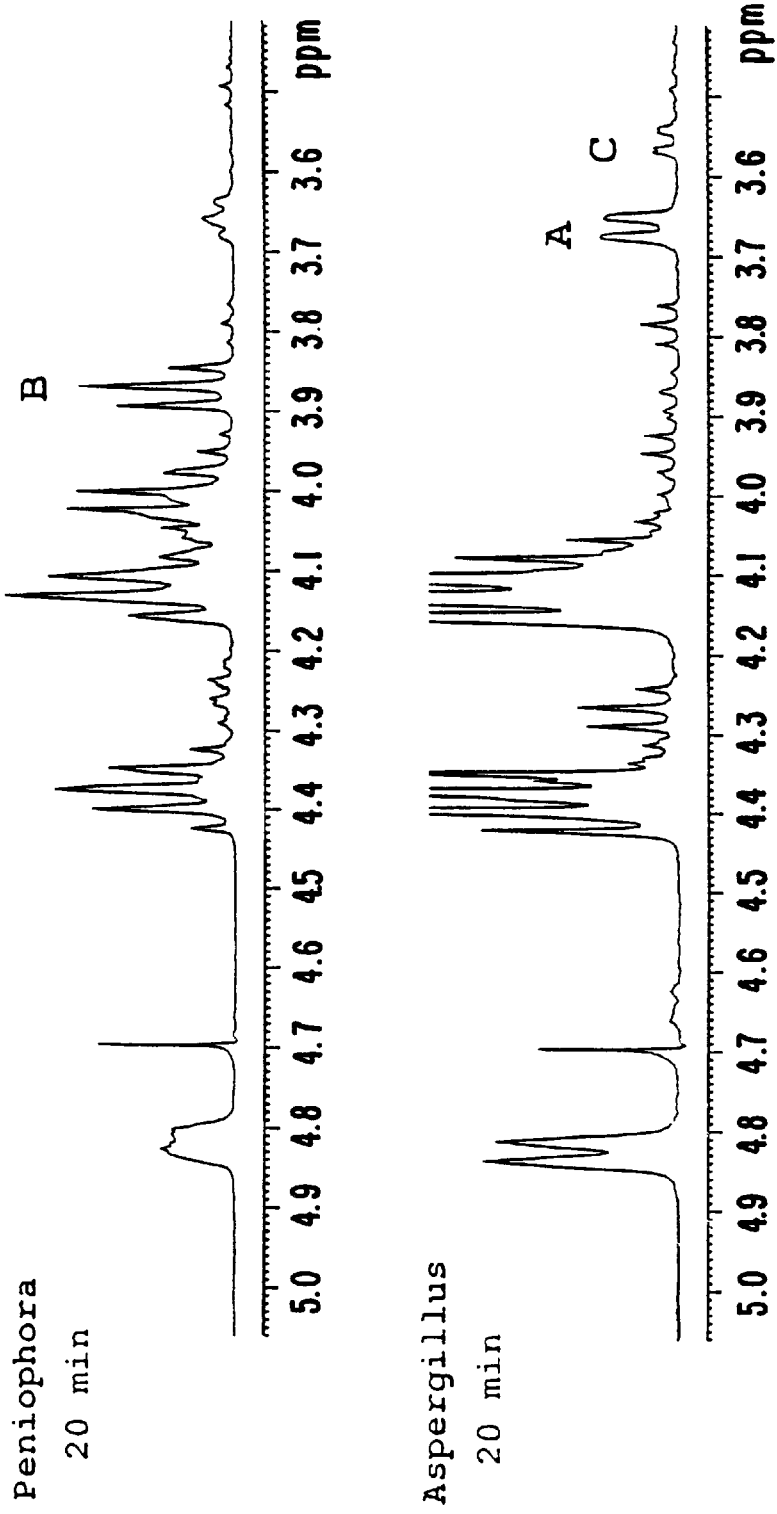

These differences are highlighted in FIG. 10*a*, which present the profiles observed after 20 min at pH 5.5 with the above indicated diagnostic signals (A,B,C) labelled.

Figure 10B:
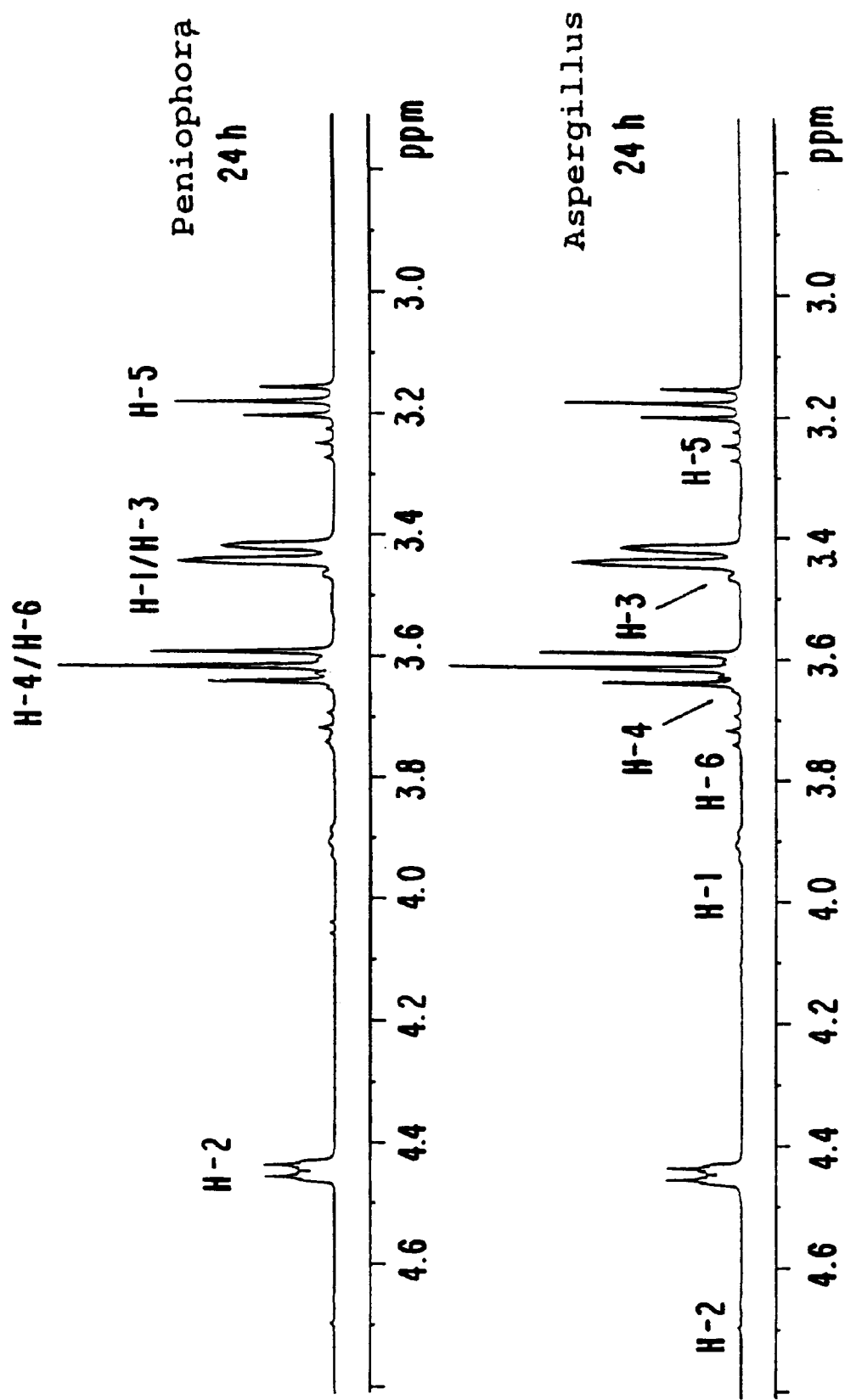

FIG. 10*b* shows the final result (under these conditions) of the hydrolysis of phytic acid at pH 5.5 (i.e. corresponding to the upper line of FIGS. 6 and 7). All signals labelled at the upper Peniophora embodiment represent the compound Ins (2)P, viz. the protons thereof, from the right to the left: H-5, H1 and H3, H4 and H6 and finally H-2. Relative intensity: 1:2:2:1. The corresponding signals are found in the bottom embodiment of Aspergillus. This means that the end product is in both embodiments Ins(2)P. However, a minor amount of Ins(1,2)$P_2$ is also detected in both embodiments, the corresponding peaks being indicated at the Aspergillus embodiment only.

Figure 11:
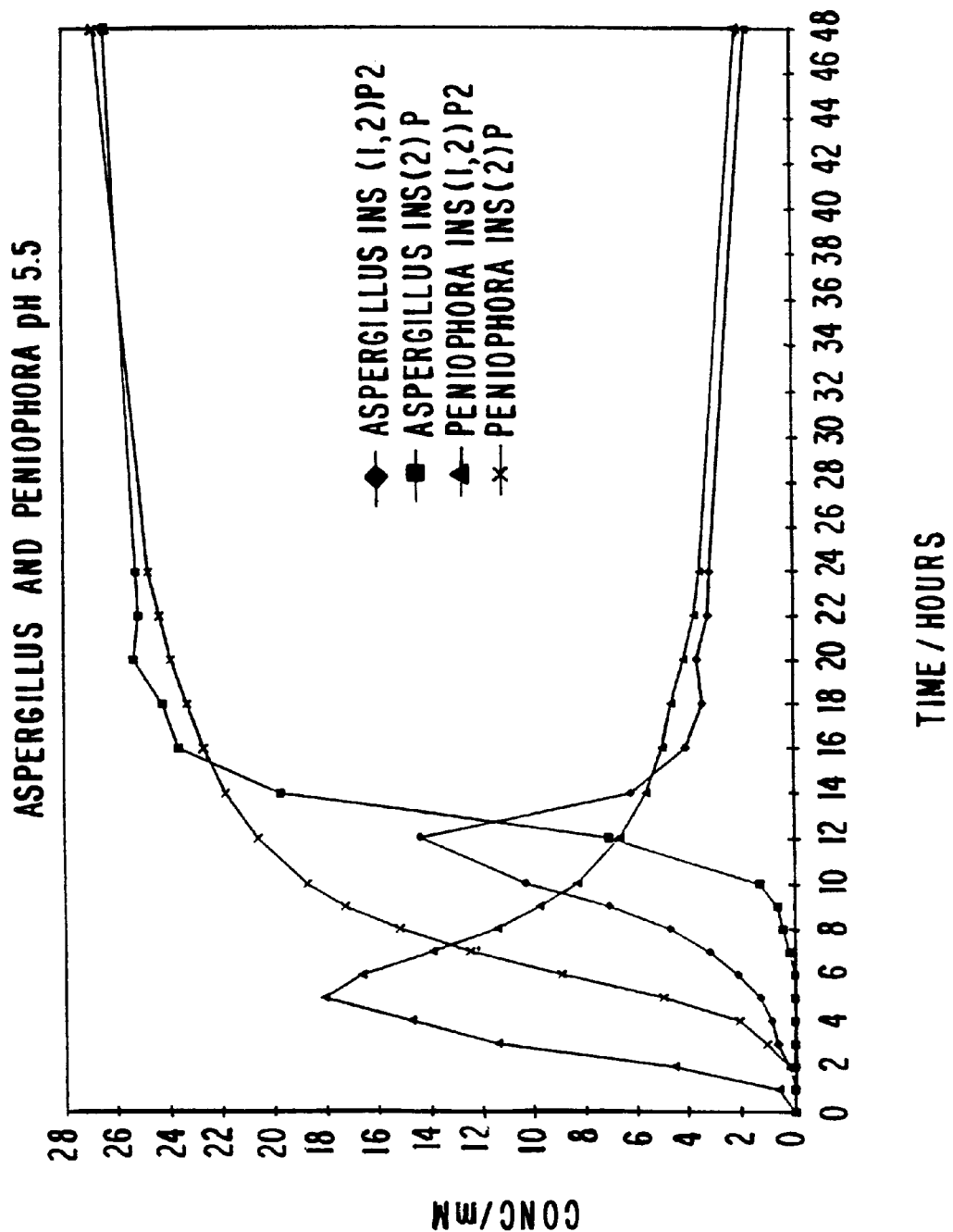

Marked differences are observed:

Aspergillus: The initial major product was identified as Ins(1,2,4,5,6)$P_5$ (A) followed by appearance of Ins(1,2,5,6) $P_4$ (C), and Ins(1,2,6)$P_3$ (D) (H-3 at $\delta 3.49(dd)$) after 1½ hours) corresponding to consecutive removal of the phosphate groups in the 3-, 4- and 5-positions. The concentration of Ins(1,2)$P_2$ (E) builds up slowly starting at 4 hours and decreases very steeply between 12 and 14 hours with a concomitant rapid increase of the Ins(2)P (F) level. This is visualized in FIG. 11 representing the time dependent concentration of Ins(1,2)$P_2$ and Ins(2)P, respectively, determined by measuring the area under the signals corresponding to H-S in Ins(1,2)$P_2$ ($\delta 3.25(t)$) and Ins(2)P ($\delta 3.18$ (t)), respectively, relative to the area under the signals corresponding to the substrates (t=0).

Peniophora: At pH 5.5 only the 6-position is initially attacked. A characteristic feature is that PA is digested at a faster rate compared to the Aspergillus phytase. Additional characteristic features are that the end product, Ins(2)P (F) appear very early (3 hours) and builds up slowly, in contrast to the very steep increase in the Ins(2)P-level towards the end of the reaction observed for the *Aspergillus phytase*.

FIG. 10*c* is a plot similar to FIG. 10*a*, but at pH 3.5. Surprisingly, at this pH the Peniophora phytase turns up to have high initial affinity to the 6- as well as the 3-position of PA (B as well as A are observed), probably with a slight preference for the 6-position.

The data generated permit i.a. the following conclusions:

At pH 5.5 as well as 3.5 the *Aspergillus phytase* attacks with a high degree of selectivity PA in the 3-position, whereas the *Peniophora phytase* at pH 5.5 with a high degree of selectivity attacks PA in the 6-position, at pH 3.5 however it seems to hydrolyze the phosphate groups at the 3- and 6-positions at comparable rates.

At pH 5.5, the *Peniophora phytase* digests PA at a faster rate compared to the *Aspergillus phytase*.

The end-product is, at pH 3.5 as well as 5.5, under the conditions applied, Ins(2)P (F).

The overall reaction rates (PA→Ins(2)P) were comparable, approximately 20 hours (FIG. 11; pH 5.5).

Accordingly, the *Aspergillus phytase* prove to be an essentially clean 3-phytase, whereas the *Peniophora phytase* at pH 5.5 appear to be an essentially clean 6-phytase and at pH 3.5 a phytase of a hitherto unknown type, viz a 3+6-phytase.

Example 6

Comparative assay, Aspergillus and *Peniophora phytase* Release of inorganic phosphate from corn The present example gives a simple assay for the phytase catalyzed liberation of phosphorous from corn at pH 3.5 and 5.5. Two parameters have been focused on—velocity and level of P-liberation.

Materials and methods:

Corn was obtained from North Carolina State University (sample No. R27), and ground at a mill (Bühler Universal) at point 6.8.

A corn-suspension (16.7% w/w) was prepared by weighing 20 g of ground corn into a 250 ml blue cap bottle and adding 100 ml of buffer.

The following buffer was used:

pH 5.5: 0.22 M acetate-buffer

The pH value of 3.5 was adjusted by 8N HCl/NaOH.

Enzymes tested: Two phytases was tested: A commercial phytase of *Aspergillus niger* (Phytase Novo®) and a *Peniophora phytase* of the invention, purified as described in example 3 and 4.

Dosage: All enzymes were applied at 25 FYT/20 g corn (correspond to 1250 FYT/kg).

The bottles with the corn suspension were closed by caps, and immediately placed in a water bath at 37° C. and subjected to constant stirring. pH was measured at this stage and again after 24 hours. After 30 min of stirring a sample of 5 ml was collected.

Then the phytase enzymes were added at a dosage of 25 FYT/20 g of corn.

Samples were then collected 5, 10, 15, 20, 25, 30, 40, 50, 60 and 120 min after the addition of the phytases, and the content of released P determined as follows:

Phytase containing samples were diluted 1+4 in buffer. Then the samples were centrifuged at 3000 rpm for 5 min, and 1.0 ml of the supernatant was collected. 2.0 ml buffer and 2.0 ml MoV stop solution (cfr. the FYT assay of Example 6) was added. The samples were placed in a refrigerator at 3–5° C. until all samples could be measured at the spectrophotometer at 415 nm.

pH was measured at time 0 and 20 hours.

For the determinations a phosphate standard or stock solution of 50 mM was used prepared. 0.5, 1.0, 1.5 and 2.0 ml stock solution is diluted to a total volume of 50 ml using buffer. 3.0 ml of each solution is added 2.0 ml MoV stop solution.

Figure 12:
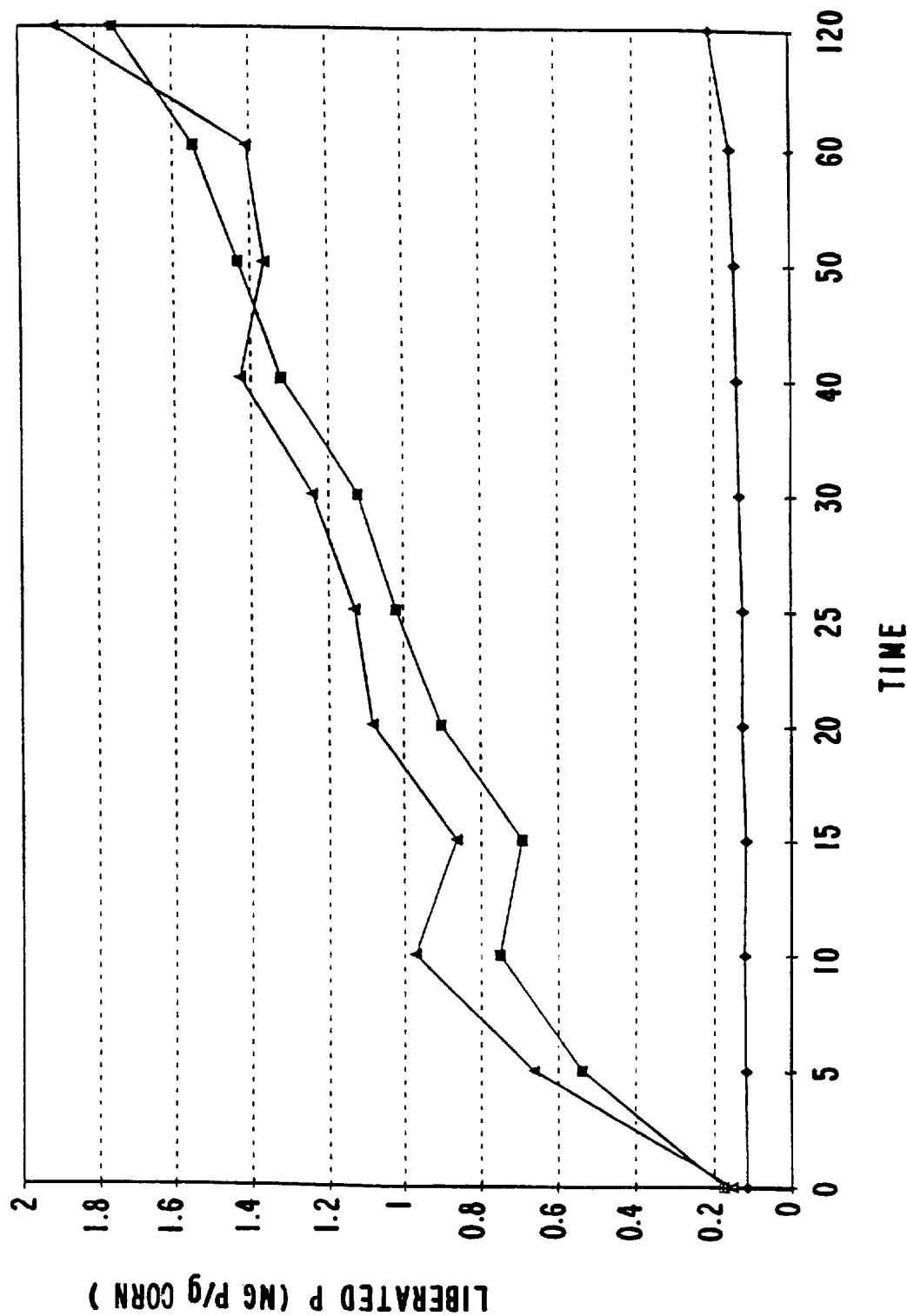
Figure 13:
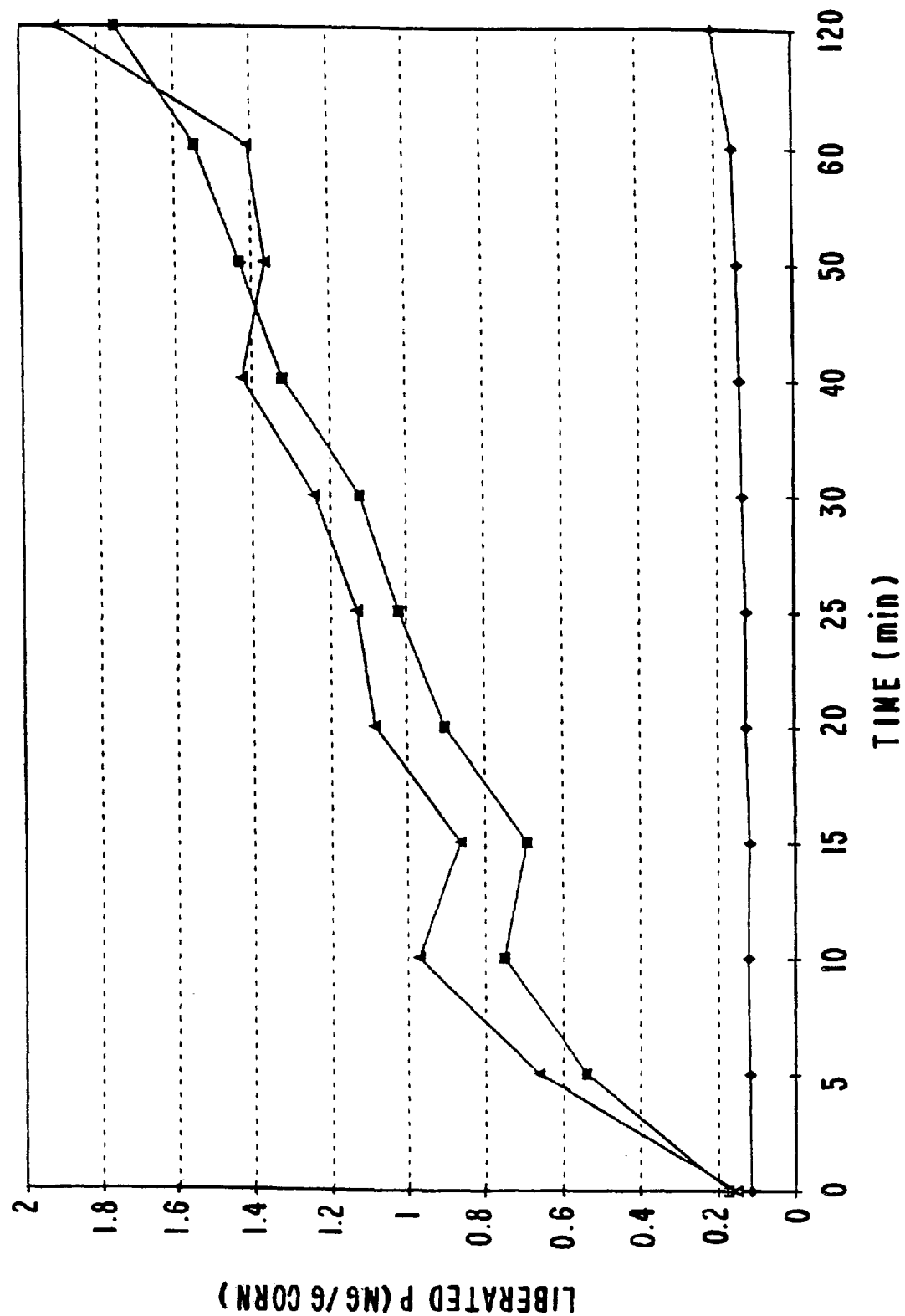

Two experiments were conducted: at pH 5.5 and at pH 3.5. The analysis results are shown at FIGS. 12 and 13 (pH 5.5 and 3.5, respectively). At these figures, symbol "♦" represents the control experiment, "▲" the Peniophora phytase and "■" the *Aspergillus phytase*.

Results and discussion:

FIG. 12 (pH 5.5) shows, that at this pH the *Peniophora phytase* liberates P from corn at significantly improved rate as compared to the *Aspergillus phytase*.

From FIG. 13 (pH 3.5) it is clearly apparent that at this pH the *Peniophora phytase* is much faster in the liberation of phosphorous from ground corn as compared to the *Aspergillus phytase* (0–120 minutes).

The passage time of the digestive system of for instance chickens/broilers is normally is of the order of magnitude of 30 minutes to 2 hours, so the observed difference is for sure important, whatever the pH. Nevertheless the pH value of 3.5 is more relevant in this respect than the pH 5.5 value.

This implies that the Peniophora enzyme is surprisingly more efficient than the known *Aspergillus phytase* as a P-liberator in the digestive system of e.g. broilers.

We claim:

1. An isolated polypeptide exhibiting phytase activity, wherein said polypeptide is selected from the group consisting of:
   (a) a polypeptide encoded by a phytase-encoding part of
      (i) SEQ ID NO: 1, or
      (ii) the DNA sequence cloned into plasmid PYES 2.0 present in *Eschericia coli* DSM 11312, and
   (b) a polypeptide which is at least 90% homologous to the polypeptide of (a) and which exhibits phytase activity, when homology is determined by GAP (version 8) using a GAP creation penalty of 5.0 and a GAP extension penalty of 0.3.

2. An isolated polypeptide exhibiting phytase activity and comprising the amino acid sequence of ammo acid no. 31 to 439 of SEQ ID NO:2 or an amino acid sequence which is at least 90% homologous to this sequence, when homology is determined by GAP (version 8), using a GAP creation penalty of 5.0 and a GAP extension penalty of 0.3.

3. An isolated polypeptide exhibiting phytase activity and comprising the amino acid sequence of SEQ ID NO:2 or an amino acid sequence which is at least 90% homologous to this sequence, when homology is determined by GAP (version 8). using a GAP creation penalty of 5.0 and a GAP extension penalty of 0.3.

4. A composition comprising the polypeptide of claim 3.

5. The composition according to claim 4 which is suitable for use in food or feed preparations.

6. The composition according to claim 4 which is an animal feed additive.

7. A feed or food comprising at least one isolated polypeptide of claim 3.

8. A process for preparing a feed or food according to claim 7, wherein said at least one isolated polypeptide is added to the food or feed components.

9. A process for reducing phytate levels in animal manure comprising feeding an animal with an effective amount of the feed according to claim 7.

10. A process for improving the food or feed utilization comprising the step of adding the polypeptide of claim 3 to feed or food components.

11. A process for liberating inorganic phosphate from phytate which process comprises the step of adding the polypeptide of claim 3 to a phytate containing material.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
ATGGTTTCTT CGGCATTCGC ACCTTCCATC CTACTTAGCT TGATGTCGAG TCTTGCTTTG      60

AGCACGCAGT TCAGCTTTGT TGCGGCGCAG CTACCTATCC CCGCACAAAA CACAAGTAAT     120

TGGGGGCCTT ACGATCCCTT CTTTCCCGTC GAACCGTATG CAGCTCCGCC GGAAGGGTGC     180

ACAGTGACAC AGGTCAACCT GATTCAGAGG CACGGCGCGC GTTGGCCCAC ATCCGGCGCG     240

CGGTCGCGGC AGGTCGCCGC CGTAGCGAAG ATACAAATGG CGCGACCATT CACGGATCCC     300

AAGTATGAGT TCCTCAACGA CTTCGTGTAC AAGTTCGGCG TCGCCGATCT GCTACCGTTC     360

GGGGCTAACC AATCGCACCA AACCGGCACC GATATGTATA CGCGCTACAG TACACTATTT     420

GAGGGCGGGG ATGTACCCTT TGTGCGCGCG GCTGGTGACC AACGCGTCGT TGACTCCTCG     480

ACGAACTGGA CGGCAGGCTT TGGCGATGCT TCTGGCGAGA CTGTTCTCCC GACGCTCCAG     540

GTTGTGCTTC AAGAAGAGGG GAACTGCACG CTCTGCAATA ATATGTGCCC GAATGAAGTG     600

GATGGTGACG AATCCACAAC GTGGCTGGGG GTCTTTGCGC CGAACATCAC CGCGCGATTG     660

AACGCTGCTG CGCCGAGTGC CAACCTCTCA GACAGCGACG CGCTCACTCT CATGGATATG     720

TGCCCGTTCG ACACTCTCAG CTCCGGGAAC GCCAGCCCCT TCTGTGACCT ATTTACCGCG     780

GAGGAGTATG TGTCGTACGA GTACTACTAT GACCTCGACA AGTACTATGG CACGGGCCCC     840

GGGAACGCTC TCGGTCCTGT CCAGGGCGTC GGATACGTCA ATGAGCTGCT TGCACGCTTG     900

ACCGGCCAAG CCGTTCGAGA CGAGACGCAG ACGAACCGCA CGCTCGACAG CGACCCTGCA     960

ACATTCCCGC TGAACCGTAC GTTCTACGCC GACTTCTCGC ATGATAACAC CATGGTGCCC    1020

ATCTTTGCGG CGCTCGGGCT CTTCAACGCC ACCGCCCTCG ACCCGCTGAA GCCCGACGAG    1080

AACAGGTTGT GGGTGGACTC TAAGCTGGTA CCGTTCTCTG GACATATGAC GGTCGAGAAG    1140

CTGGCATGTT CTGGGAAGGA GGCGGTCAGG GTGCTCGTGA ACGACGCGGT GCAGCCGCTG    1200

GAGTTCTGCG GAGGTGTTGA TGGGGTGTGC GAGCTTTCGG CTTTCGTAGA GAGCCAGACG    1260

TATGCGCGGG AGAATGGGCA AGGCGACTTC GCCAAGTGCG GCTTTGTTCC GTCGGAATAG    1320
```

(2) INFORMATION FOR SEQ ID NO:2:

(i) SEQUENCE CHARACTERISTICS:
    (A) LENGTH: 439 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:2:

```
Met Val Ser Ser Ala Phe Ala Pro Ser Ile Leu Leu Ser Leu Met Ser
  1               5                  10                  15

Ser Leu Ala Leu Ser Thr Gln Phe Ser Phe Val Ala Ala Gln Leu Pro
                 20                  25                  30

Ile Pro Ala Gln Asn Thr Ser Asn Trp Gly Pro Tyr Asp Pro Phe Phe
             35                  40                  45

Pro Val Glu Pro Tyr Ala Ala Pro Pro Glu Gly Cys Thr Val Thr Gln
         50                  55                  60

Val Asn Leu Ile Gln Arg His Gly Ala Arg Trp Pro Thr Ser Gly Ala
 65                  70                  75                  80

Arg Ser Arg Gln Val Ala Ala Val Ala Lys Ile Gln Met Ala Arg Pro
                 85                  90                  95

Phe Thr Asp Pro Lys Tyr Glu Phe Leu Asn Asp Phe Val Tyr Lys Phe
                100                 105                 110

Gly Val Ala Asp Leu Leu Pro Phe Gly Ala Asn Gln Ser His Gln Thr
            115                 120                 125

Gly Thr Asp Met Tyr Thr Arg Tyr Ser Thr Leu Phe Glu Gly Gly Asp
        130                 135                 140

Val Pro Phe Val Arg Ala Ala Gly Asp Gln Arg Val Val Asp Ser Ser
145                 150                 155                 160

Thr Asn Trp Thr Ala Gly Phe Gly Asp Ala Ser Gly Glu Thr Val Leu
                165                 170                 175

Pro Thr Leu Gln Val Val Leu Gln Glu Gly Asn Cys Thr Leu Cys
            180                 185                 190

Asn Asn Met Cys Pro Asn Glu Val Asp Gly Asp Ser Thr Thr Trp
            195                 200                 205

Leu Gly Val Phe Ala Pro Asn Ile Thr Ala Arg Leu Asn Ala Ala Ala
    210                 215                 220

Pro Ser Ala Asn Leu Ser Asp Ser Asp Ala Leu Thr Leu Met Asp Met
225                 230                 235                 240

Cys Pro Phe Asp Thr Leu Ser Ser Gly Asn Ala Ser Pro Phe Cys Asp
                245                 250                 255

Leu Phe Thr Ala Glu Glu Tyr Val Ser Tyr Glu Tyr Tyr Tyr Asp Leu
                260                 265                 270

Asp Lys Tyr Tyr Gly Thr Gly Pro Gly Asn Ala Leu Gly Pro Val Gln
            275                 280                 285

Gly Val Gly Tyr Val Asn Glu Leu Leu Ala Arg Leu Thr Gly Gln Ala
        290                 295                 300

Val Arg Asp Glu Thr Gln Thr Asn Arg Thr Leu Asp Ser Asp Pro Ala
305                 310                 315                 320

Thr Phe Pro Leu Asn Arg Thr Phe Tyr Ala Asp Phe Ser His Asp Asn
                325                 330                 335

Thr Met Val Pro Ile Phe Ala Ala Leu Gly Leu Phe Asn Ala Thr Ala
            340                 345                 350

Leu Asp Pro Leu Lys Pro Asp Glu Arg Leu Trp Val Asp Ser Lys
        355                 360                 365
```

-continued

```
Leu Val Pro Phe Ser Gly His Met Thr Val Glu Lys Leu Ala Cys Ser
    370             375             380

Gly Lys Glu Ala Val Arg Val Leu Val Asn Asp Ala Val Gln Pro Leu
385             390             395             400

Glu Phe Cys Gly Gly Val Asp Gly Val Cys Glu Leu Ser Ala Phe Val
            405             410             415

Glu Ser Gln Thr Tyr Ala Arg Glu Asn Gly Gln Gly Asp Phe Ala Lys
            420             425             430

Cys Gly Phe Val Pro Ser Glu
            435

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Leu Pro Ile Pro Ala Gln Asn
1               5
```